United States Patent
Li et al.

(10) Patent No.: US 11,136,339 B2
(45) Date of Patent: Oct. 5, 2021

(54) DIHYDROARTEMISININ DIPLOID DERIVATIVE, PHARMACEUTICAL COMPOSITION THEREOF, AND APPLICATION

(71) Applicant: SOUTHEAST UNIVERSITY, Nanjing (CN)

(72) Inventors: Xinsong Li, Nanjing (CN); Ma Si, Nanjing (CN); Longbing Ling, Nanjing (CN)

(73) Assignee: SOUTHEAST UNIVERSITY, Nanjing (CN)

( * ) Notice: Subject to any disclaimer, the term of this patent is extended or adjusted under 35 U.S.C. 154(b) by 0 days.

(21) Appl. No.: 16/488,568

(22) PCT Filed: Apr. 11, 2018

(86) PCT No.: PCT/CN2018/082649
§ 371 (c)(1),
(2) Date: Sep. 25, 2019

(87) PCT Pub. No.: WO2018/157874
PCT Pub. Date: Sep. 7, 2018

(65) Prior Publication Data
US 2020/0040008 A1    Feb. 6, 2020

(30) Foreign Application Priority Data
Feb. 28, 2017  (CN) .......................... 201710115410.4

(51) Int. Cl.
*C07D 519/00*     (2006.01)
*A61P 17/06*      (2006.01)
*A61P 19/02*      (2006.01)
*A61P 33/06*      (2006.01)
*A61P 35/00*      (2006.01)
*C07F 9/655*      (2006.01)

(52) U.S. Cl.
CPC ............ *C07D 519/00* (2013.01); *A61P 17/06* (2018.01); *A61P 19/02* (2018.01); *A61P 33/06* (2018.01); *A61P 35/00* (2018.01); *C07F 9/65525* (2013.01)

(58) Field of Classification Search
CPC .................................................... C07D 519/00
USPC ........................................................ 549/367
See application file for complete search history.

(56) References Cited

U.S. PATENT DOCUMENTS

2005/0148598 A1 *  7/2005  O'Neill ................ C07D 493/18
                                              514/254.11

FOREIGN PATENT DOCUMENTS

WO     WO 2012103784     *  8/2012  ........... C07D 493/18

* cited by examiner

Primary Examiner — Nizal S Chandrakumar
(74) Attorney, Agent, or Firm — CBM Patent Consulting, LLC

(57) ABSTRACT

Disclosed are a dihydroartemisinin dimer derivative, a pharmaceutical composition, and an application thereof. The derivative is an artemisinin dimer used for drugs treating or preventing malaria caused by plasmodium, drugs treating autoimmune diseases such as lupus erythematosus, and anti-tumour drugs, which is a pharmaceutical composition prepared from the dihydroartemisinin dimer derivative and a pharmaceutically acceptable carrier.

3 Claims, 9 Drawing Sheets

DIHYDROARTEMISININ DIPLOID DERIVATIVE, PHARMACEUTICAL COMPOSITION THEREOF, AND APPLICATION

TECHNICAL FIELD

The present invention relates to a dihydroartemisinin dimer derivative, a pharmaceutical composition thereof and an application thereof in pharmacy, belonging to the field of medical technologies.

BACKGROUND

Parasitosis is a disease caused by parasite invading the human body. Pathological changes and clinical manifestations caused by different parasite species and parasitic sites are different. The disease is widely distributed in most areas of the world, and is more common in poor and backward regions with poor sanitary conditions, and more common in tropical and subtropical regions, and the infected people are mainly working people who are exposed to more epidemic sources and children with lower immunity.

Malaria is the most important parasitosis in the tropical region, and is also an infectious disease caused by plasmodium parasitizing in the human body. The patient is infected by biting of a malaria mosquito or blood transfusion from people with the plasmodium, and different plasmodia cause tertian malaria, quartan malaria, malignant malaria and oval malaria respectively. The malaria is mainly manifested as periodic and regular attacks, chill, fever and hyperhidrosis of whole body, and anemia and splenomegaly caused by repeated attacks for a long time. Jaundice, epileptic seizure, coma or death can be caused in serious cases.

The malaria is prevalent in 102 countries and regions, and according to the report of World Health Organization (WHO), 2 billion people live in endemic regions. In tropical and subtropical regions located in a broad belt around the equator, especially in some countries in Africa, Southeast Asia, Central America and South America, a mortality rate of the malignant malaria is extremely high, with Africa having the worst epidemic situation, and any resident in Africa is infected with the disease many times a year from birth to death. According to the statistics of WHO, there were a total of 198 million malaria cases in the whole world in 2013, resulting in about 800,000 deaths, 90% of which occurred in Africa.

Quinine was first used to treat malaria. Chloroquine is another effective anti-malaria drug. Since the middle of the $20^{th}$ century, some new drugs have been developed. Artemisinin, dihydroartemisinin, etc. developed by Chinese scientists have good anti-malaria effects, but water solubilities of artemisinin, dihydroartemisinin and artesunate are all very poor.

At present, the malaria has gradually developed resistance to several drugs, for example, the malignant malaria with chloroquine resistance has been spread all over the world. The resistance to the combined use of sulfadoxine and pyrimethamine has also been spread in regions with difficulty in treatment with the chloroquine in South Asia and South America. In addition, a resistance problem of artemisinin is becoming increasingly serious in some regions in Southeast Asia. In recent years, the plasmodium has generally developed resistance to the artemisinin, the most effective anti-malaria drug, in western and northern regions in Cambodia, Thailand, Vietnam and eastern region in Myanmar; and the plasmodium has also begun to show resistance to the artemisinin in central region of Myanmar, southern region of Laos and northeastern region of Cambodia. Today's resistance to multiple existing anti-malaria drugs is very terrible. The recommended treatment for the malaria is the artemisinin combined with another anti-malaria drug, comprising mefloquine, benflumetol or sulfadoxine/pyrimethamine. Therefore, it is necessary to invent an effective anti-malaria drug to overcome drug resistance, improve water solubility and enhance drug efficacy.

The autoimmune disease is a disease caused by the damage to an autotissue led by an immune reaction of a body to an autoantigen. The disease mainly comprises chronic lymphocytic thyroiditis, hyperthyroidism, insulin-dependent diabetes mellitus, myasthenia gravis, chronic ulcerative colitis, pernicious anemia with chronic atrophic gastritis, goodpastures syndrome, pemphigus vulgaris, pemphigoid, primary biliary cirrhosis, multiple sclerosis, acute idiopathic polyneuritis, etc. There is also systemic autoimmune disease, such as systemic lupus erythematosus, Sjogren's syndrome, rheumatoid arthritis, ankylosing spondylitis, scleroderma, polyarteritis nodosa, Wegener granulomatosis, etc.

The autoimmune disease is caused by reduction or deletion of an immune function led by congenital hypoplasia or acquired damage of an immune system. Primary immunodeficiency disease is an immunodeficiency disease caused by damage to the immune system during development due to genetic factors or congenital factors. The primary immunodeficiency disease comprises B cell deficiency disease, T cell deficiency disease, T cell and B cell combined deficiency disease, phagocyte deficiency disease and complement system deficiency disease. Secondary immunodeficiency disease is an immunodeficiency disease caused by immune system dysfunction due to acquired factors. The disease can be secondary to tumors, the use of immunosuppressants or infectious diseases. Most autoimmune diseases do not have good therapeutic drugs.

The systemic lupus erythematosus (SLE) is an autoimmune disease involving many systems and organs, and produces a variety of autoantibodies due to cellular and humoral immune dysfunction. It can affect skin, serosa, joint, kidney, central nervous system, etc., and is characterized by autoimmunity, and there are many autoantibodies in a body of a patient, which not only affect humoral immunity, but also affect cellular immunity, and a complement system is also changed. The pathogenesis is mainly formed by immune complexes. The exact cause of disease is unknown. The patient's condition is an alternating process of repeated attacks and remissions.

The rheumatoid arthritis is also a chronic and systemic autoimmune disease mainly dominated by inflammatory synovitis with unclear cause of disease. It is characterized by multiple joints of small joints of hands and feet, symmetry and invasive joint inflammation, often accompanied by involvement of extra-articular organs and positive serum rheumatoid factor, which can lead to joint deformity and loss of function. The inflammation can cause joint deformation and even disability, and a part of mobility can be lost due to joint pain and wear. The disease can also systematically affect other extra-articular tissues, comprising skin, blood vessels, heart, lungs and muscles.

The artemisinin is found to have certain curative effects on systemic lupus erythematosus and rheumatoid arthritis from previous studies, but the effect is not very ideal. Therefore, it is necessary to invent a more effective anti-autoimmune disease drug to improve the drug efficacy.

An artemisinin dimer combines artemisinins of two molecules together through a linking group, which can certainly improve the anti-malaria drug efficacy. However, there have been no reports of amphiphilic molecules of the artemisinin dimer so far, nor have there been reports of assembling the amphiphilic molecules of the artemisinin dimer into nanoparticles.

SUMMARY

Technical problem: the present invention provides a dihydroartemisinin dimer derivative with excellent water solubility, self-assembly and co-assembly capabilities, improved drug encapsulation efficiency, low toxicity, easy phagocytosis by cells and targeted effect, and a pharmaceutical composition thereof, which can play a role in treating or preventing parasitoses, autoimmune diseases, leukemia and tumors. The present invention also provides a pharmaceutical composition of the dihydroartemisinin dimer derivative and an application thereof in anti-parasitosis drugs, anti-autoimmune disease drugs, leukemia drugs and anti-tumor drugs.

Technical solution: a dihydroartemisinin dimer derivative according to the present invention is a compound with the following general formula (1) or a pharmaceutically acceptable salt of the compound of the general formula (1):

in the formula (1), Y is a substituent with the following structure:

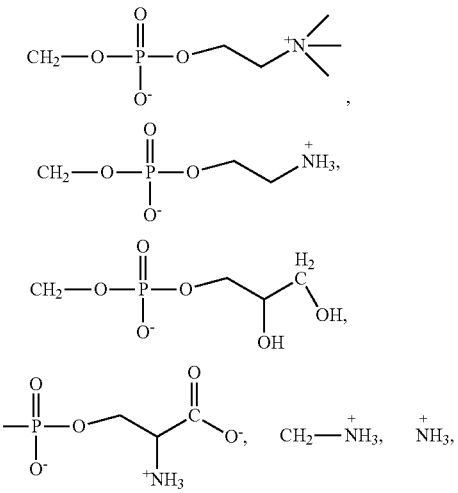

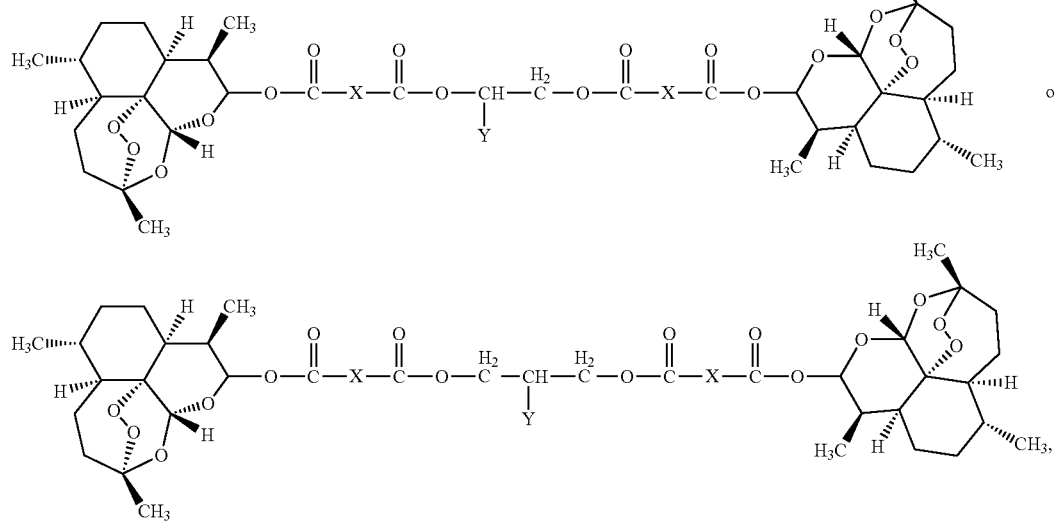

formula (1)

wherein X is the following group:
CH$_2$, CH$_2$—CH$_2$, CH$_2$—CH$_2$—CH$_2$, CH$_2$—CH$_2$—CH$_2$—CH$_2$, CH$_2$—S—S—CH$_2$, CH$_2$—CH$_2$—S—S—CH$_2$—CH$_2$, CH$_2$—O—CH$_2$, O—CH$_2$—CH$_2$—O, O—CH$_2$—CH$_2$—CH$_2$—O, O—CH$_2$—CH$_2$—CH$_2$—CH$_2$—O, O—CH$_2$—CH$_2$—O—CH$_2$—CH$_2$—O, O—CH$_2$—CH$_2$—O—CH$_2$—CH$_2$—O—CH$_2$—CH$_2$—O, O—CH$_2$—CH$_2$—SS—CH$_2$—CH$_2$—O—CO—CH$_2$—CH$_2$, O—CH$_2$—CH$_2$—CH$_2$—CH$_2$—O—CO—CH$_2$—CH$_2$, O—CH$_2$—CH$_2$—CH$_2$—CH$_2$—CH$_2$—CH$_2$—O—CO—CH$_2$—CH$_2$, O—CH$_2$—CH$_2$—CH$_2$—O—CO—CH$_2$—CH$_2$, O—CH$_2$—CH$_2$—O—CO—CH$_2$—CH$_2$, NH—CH$_2$—CH$_2$—NH, NH—CH$_2$—CH$_2$—CH$_2$—NH, NH—CH$_2$—CH$_2$—CH$_2$—CH$_2$—NH, NH—CH$_2$—CH$_2$—CH$_2$—CH$_2$—CH$_2$—NH, NH—CH$_2$—CH$_2$—CH$_2$—CH$_2$—CH$_2$—CH$_2$—NH, O—CH$_2$—CH$_2$—S—S—CH$_2$—CH$_2$—O or NH—CH$_2$—CH$_2$—S—S—CH$_2$—CH$_2$—NH;

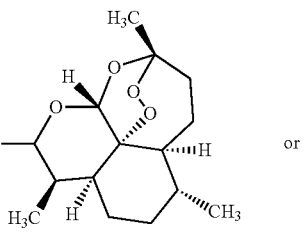

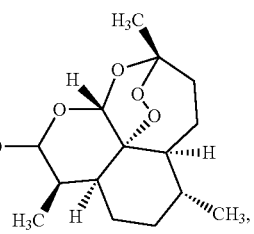

-continued

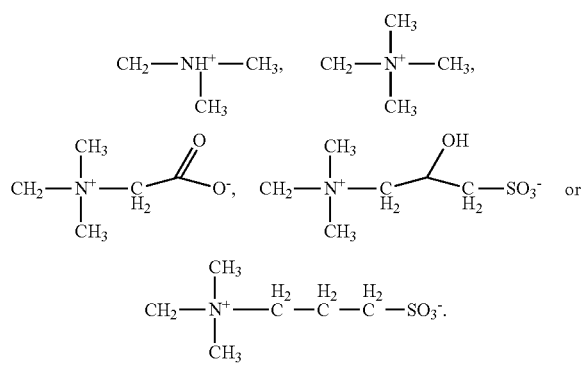

According to the dihydroartemisinin dimer derivative of the present invention, the compound of the general formula (1) above is formed by connecting two dihydroartemisinin molecules by a linker containing cations, anions or both cations and anions through a chemical bond.

A pharmaceutical composition of the dihydroartemisinin dimer derivative according to the present invention comprises the dihydroartemisinin dimer derivative, or the dihydroartemisinin dimer derivative and a pharmaceutically acceptable carrier, or the dihydroartemisinin dimer derivative and a synergist.

The pharmaceutical composition of the present invention is a liquid preparation, a solid preparation, a semi-solid preparation, a capsule, a granule, a gel, an injection, a sustained release preparation or a controlled release preparation.

The pharmaceutical composition of the present invention is nanoparticles with a particle size of 10 nm to 1000 nm.

According to an application of the dihydroartemisinin dimer derivative of the present invention and the pharmaceutical composition thereof in preparation of anti-parasitosis drugs, anti-autoimmune disease drugs and anti-tumor drugs, the application is to prepare the dihydroartemisinin dimer derivative or the pharmaceutically acceptable salt thereof, or the dihydroartemisinin dimer derivative and the synergist into the pharmaceutical composition with the pharmaceutically acceptable carrier.

According to the application of the dihydroartemisinin dimer derivative of the present invention and the pharmaceutical composition thereof in preparation of drugs for treating or preventing parasitoses, autoimmune diseases, tumors, leukemia and skin diseases, the application is to prepare the dihydroartemisinin dimer derivative or the pharmaceutically acceptable salt thereof, or the dihydroartemisinin dimer derivative and the synergist into the pharmaceutical composition with the pharmaceutically acceptable carrier.

The dihydroartemisinin dimer derivative of the present invention and the pharmaceutical composition thereof are applied in preparation of drugs for treating or preventing malaria, schistosomiasis, toxoplasmosis, leishmaniasis, filariasis or ancylostomiasis.

The dihydroartemisinin dimer derivative of the present invention and the pharmaceutical composition thereof are applied in preparation of drugs for treating or preventing systemic lupus erythematosus, rheumatoid arthritis, systemic vasculitis, pemphigus, mixed connective tissue disease, autoimmune hemolytic anemia, thyroid autoimmune disease or ulcerative colitis.

The drugs for treating or preventing malaria caused by plasmodium, the drugs for treating autoimmune diseases and the anti-tumor drugs are pharmaceutical compositions prepared from the dihydroartemisinin dimer derivative above and the pharmaceutically acceptable carrier.

The drugs for treating or preventing malaria caused by plasmodium, the drugs for treating autoimmune diseases and the anti-tumor drugs are medicaments prepared from the pharmaceutical compositions prepared from the dihydroartemisinin dimer derivative above and the pharmaceutically acceptable carrier.

The drugs for treating or preventing parasitoses caused by parasite, the drugs for treating autoimmune diseases, the leukemia drugs and the anti-tumor drugs are medicaments prepared from the pharmaceutical compositions prepared from the dihydroartemisinin dimer derivative above, the synergist and the pharmaceutically acceptable carrier.

In a preferred solution of the pharmaceutical composition of the present invention, the pharmaceutical composition is liposomal nanoparticles with a particle size of 10 nm to 1000 nm, and the pharmaceutical composition also comprises an auxiliary agent. The auxiliary agent is preferably phospholipid and cholesterol.

The dihydroartemisinin dimer derivative of the present invention can exist in a form of isomer, comprising all possible stereoisomers and mixtures of two or more isomers.

The pharmaceutical composition of the compound of the present invention can be prepared according to a method commonly known in the art. For this purpose, if necessary, the compound of the present invention or the compound of the present invention combined with one or more solid or liquid pharmaceutical excipients and/or adjuvants can be prepared into an appropriate application form or dosage form for administration.

The compound of the present invention or the pharmaceutical composition containing the compound can be administered in unit dosage form, and an administration route can be an enteral route or a parenteral route, such as oral administration, intramuscular administration, subcutaneous administration, nasal administration, oral mucosa administration, skin administration, peritoneal administration or rectal administration.

The administration route of the compound of the present invention or the pharmaceutical composition containing the compound can be injection administration, comprising intravenous injection, intramuscular injection, subcutaneous injection, intradermal injection, acupoint injection, etc. An administration dosage form can be a liquid dosage form or a solid dosage form. For example, the liquid dosage form can be a true solution, a colloid, a microparticle dosage form, an emulsion dosage form and a suspension dosage form. Other dosage forms comprise tablet, capsule, dropping pill, aerosol, pill, powder, solution, suspension, emulsion, granule, suppository, lyophilized powder for injection, etc.

The compound of the present invention can be prepared into common preparation, and can also be prepared into slow release preparation, controlled release preparation, targeted preparation and various microparticle administration systems. In order to prepare the compound into various dosage forms, various carriers commonly known in the art can be widely used.

The compound of the present invention is prepared into injection preparation, such as solution, suspension solution, emulsion and freeze-dried powder injection, and the preparation can be aqueous or non-aqueous, and can contain one or more pharmaceutically acceptable carriers, diluents, adhesives, lubricants, preservatives, surfactants or dispersants. For example, the diluent can be selected from water, ethanol, polyethylene glycol, 1,3-propylene glycol, ethoxylated isostearyl alcohol, polyoxidized isostearyl alcohol, polyoxyethylene sorbitan fatty acid ester, phospholipid, etc.

Nanoparticles prepared from the compound of the present invention have a particle size of 10 nm to 1000 nm.

Liposomal nanoparticles prepared from the compound of the present invention have an average particle size of 10 nm to 1000 nm. Liposomal nanoparticles prepared from the compound of the present invention and the auxiliary agent has a particle size of 10 nm to 1000 nm, and the auxiliary agent used is phospholipid. The auxiliary agent also contains a targeted group folic acid, a galactose, an antibody, a biotin or a polypeptide. For the liposome nanoparticles prepared from the compound of the present invention, or the compound of the present invention and the auxiliary agent, the liposomal nanoparticles is loaded with a synergist and has a particle size of 10 nm to 1000 nm.

The liposomal nanoparticles of the pharmaceutical composition of the present invention are liquid preparation, solid preparation, semi-solid preparation, capsule, granule, gel, injection, sustained release preparation or controlled release preparation.

In terms of activity screening, the compound of the present invention or the composition shows a good parasite killing effect. The test shows that the compound of the present invention has no obvious in-vivo toxicity. Therefore, the compound can be used as anti-parasitosis drugs for animals, and is preferably used for mammals, especially human beings.

In terms of activity screening, the compound of the present invention or the composition shows a good plasmodium killing effect. The test shows that the compound of the present invention has no obvious in-vivo toxicity. Therefore, the compound can be used as anti-malaria drugs for animals, and is preferably used for mammals, especially human beings.

The compound of the present invention or the composition shows a good anti-tumor effect. The test shows that the compound of the present invention has no obvious in-vivo toxicity. Therefore, the compound can be used as anti-treatment drugs for human beings.

The compound of the present invention or the composition shows treatment to autoimmune diseases. The test shows that the compound of the present invention has no obvious in-vivo toxicity. Therefore, the compound can be used as drugs for treating autoimmune diseases for human beings.

The compound of the present invention or the composition shows treatment to systemic lupus erythematosus. The test shows that the compound of the present invention has no obvious in-vivo toxicity. Therefore, the compound can be used as drugs for treating systemic lupus erythematosus for human beings.

The compound of the present invention or the composition shows treatment to rheumatoid arthritis. The test shows that the compound of the present invention has no obvious in-vivo toxicity. Therefore, the compound can be used as drugs for treating rheumatoid arthritis for human beings.

A preparation method of peroxide liposomal nanoparticles of the present invention is that the peroxide liposomal nanoparticles are prepared from a peroxide of the compound of the present invention or a mixture of the compound of the present invention and the auxiliary agent through methods such as a film dispersion method, a reverse phase evaporation method, a freeze drying method, an ultrasonic dispersion method, a spray drying method, a film extrusion method and a high-pressure homogenization method.

The dihydroartemisinin dimer derivative of the present invention contains two peroxy groups and anion, cation or zwitterion groups, with good hydrophilicity and water solubility; the peroxide is prepared into the nanoparticles according to the present invention, with a property of a liposome and a property of forming liquid preparation, solid preparation, semi-solid preparation, sterilization preparation and aseptic preparation; the dihydroartemisinin dimer derivative of the present invention and the pharmaceutical composition thereof are used for anti-malaria drugs, drugs for treating autoimmune diseases and drugs for treating tumors; and the dihydroartemisinin dimer derivative of the present invention and the pharmaceutical composition thereof have drug resistance without obvious toxic and side effects.

Beneficial effects: compared with the prior art, the present invention has the following advantages.

The present invention relates to a dihydroartemisinin dimer derivative with two peroxide bridges, and a purpose of the compound in preparation of drugs for preventing and treating malaria and autoimmune diseases and anti-tumor drugs is disclosed by the present invention for the first time. The dihydroartemisinin dimer derivative of the present invention is the compound with the following general formula (1) formed by connecting two dihydroartemisinin molecules by the linker containing cations, anions or both cations and anions through the chemical bond or the pharmaceutically acceptable salt of the compound of the general formula (1):

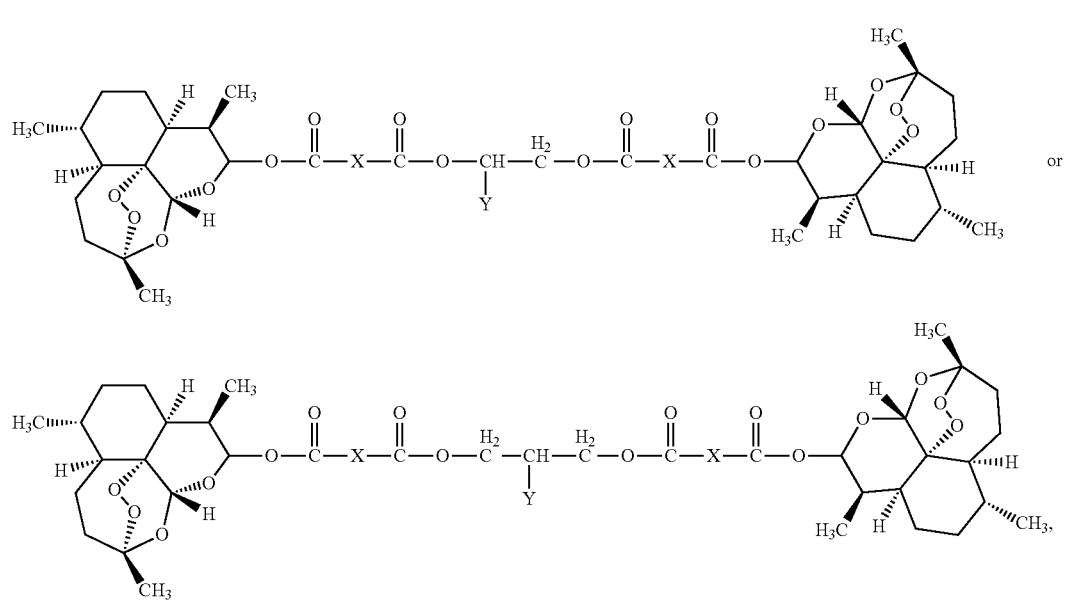

formula (1)

wherein a specific structure of X refers to the technical solution; Y is a hydrophilic substituent containing cations, anions, or both cation and anion structures, and the specific structure refers to the technical solution. The structure of the formula (1) contains a hydrophilic head part Y, so that the peroxide has excellent water solubility and self-assembly and co-assembly capabilities;

two dioxygen bonds (OO) of the dihydroartemisinin dimer derivative of the present invention directly release peroxy radicals in an in-vivo environment to play a role in treating or preventing parasitoses, autoimmune diseases, tumors, leukemia and skin diseases;

two dioxygen bonds (OO) of the dihydroartemisinin dimer derivative of the present invention directly release peroxy radicals in an in-vivo environment to play a role in treating or preventing malaria, toxoplasmosis, systemic lupus erythematosus, rheumatoid arthritis and leukemia;

the dihydroartemisinin dimer derivative of the present invention controls the release of artesunate or dihydroartemisinin in vivo;

the dihydroartemisinin dimer derivative of the present invention has anti-drug resistance; and the dihydroartemisinin dimer derivative of the present invention has anti-plasmodium resistance;

the dihydroartemisinin dimer derivative of the present invention and the pharmaceutical composition thereof play a role in treating parasitoses, tumors, leukemia, autoimmune diseases and skin diseases;

the dihydroartemisinin dimer derivative of the present invention and the pharmaceutical composition thereof play a role in treating malaria, toxoplasmosis, tumors, systemic lupus erythematosus and rheumatoid arthritis;

the dihydroartemisinin dimer derivative of the present invention is the hydrophilic substituent containing cations, anions or both cation and anion structures with amphiphilicity, which can be self-assembled or co-assembled with phospholipid to form stable nanoparticles, overcomes the defect that drugs are easy to leak when being generally wrapped by nanoparticles, and simultaneously improves a drug wrapping efficiency;

the liposome or the nanoparticles assembled from the dihydroartemisinin dimer derivative of the present invention or the composition prolongs a release time and an action time of the dihydroartemisinin dimer derivative, and the dihydroartemisinin dimer derivative of the present invention or the composition is easy to enter cells in the form of liposome or nanoparticles to exert a drug efficacy;

the liposomal nanoparticles assembled from the dihydroartemisinin dimer derivative of the present invention or the composition has anti-drug resistance; and the liposomal nanoparticles assembled from the dihydroartemisinin dimer derivative of the present invention or the composition has anti-plasmodium resistance;

the dihydroartemisinin dimer derivative of the present invention or the composition can be very easily self-assembled into the liposome or the nanoparticles by the thin film method, etc., with the particle size of 10 nm to 1000 nm; and the liposome or the nanoparticles assembled from the dihydroartemisinin dimer derivative of the present invention or the composition can be loaded with the synergist to improve a drug efficacy;

the liposome nanoparticles of the dihydroartemisinin dimer derivative of the present invention have a liposome structure similar to a cell membrane structure, is prone to phagocytosis by cells, releases active drug molecules, and plays a role in resisting parasitoses, tumors and autoimmune diseases;

the liposome nanoparticles of the dihydroartemisinin dimer derivative of the present invention have the liposome structure similar to the cell membrane structure, is prone to phagocytosis by cells, and has a passive targeting effect;

the dihydroartemisinin dimer derivative of the present invention or the pharmaceutical composition of the dihydroartemisinin dimer derivative of the present invention and a conventional pharmaceutical carrier has a low toxicity;

the dihydroartemisinin dimer derivative of the present invention and the liposome nanoparticles thereof can be used as liquid preparation, solid preparation, semi-solid preparation, sterilization preparation and sterile preparation, and can form a liposome or nanoparticles solution in water phase systems such as water, phosphoric acid buffer solution, and citrate buffer solution;

the peroxide liposome of the present invention is combined with the auxiliary agent containing a targeting group and has an active targeting effect;

the dihydroartemisinin dimer derivative of the formula (1) of the present invention and the liposome nanoparticles thereof are simple in a preparation process;

the dihydroartemisinin dimer derivative of the formula (1) of the present invention and the liposome nanoparticles thereof are also a new prodrug, which can directly exert a drug efficacy in vivo or exert a drug efficacy through hydrolysis, can prolong a half-life of drug release, and has lower toxic and side effects; and the dihydroartemisinin dimer derivative of the general formula (1) of the present invention and the pharmaceutically acceptable salt containing counter ions and formed by the compounds, and the composition thereof have an anti-malaria effect and can overcome the defect of drug resistance of plasmodium caused by common artemisinin, that is, the dihydroartemisinin dimer derivative of the general formula (1) of the present invention or the pharmaceutical composition is applied for anti-malaria drugs without causing drug resistance of parasite, and has a good killing effect on artemisinin-resistant plasmodium.

DETAILED DESCRIPTION

Figure 1:
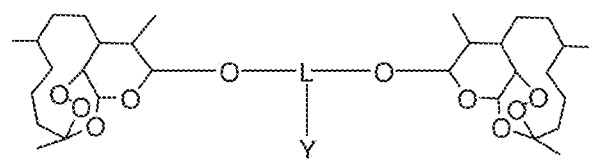
FIG. 1 illustrates a general structure formula of a dihydroartemisinin dimer derivative according to the present invention.

The technical solutions of the present invention are further described in detail below with reference to the drawings and the embodiments.

The dihydroartemisinin dimer derivative of the present invention is the compound with the following general formula (1) formed by connecting two dihydroartemisinin molecules by the linker containing cations, anions or both cations and anions through the chemical bond or the pharmaceutically acceptable salt of the compound of the general formula (1):

wherein X is the following group: $CH_2$, $CH_2-CH_2$, $CH_2-CH_2-CH_2$, $CH_2-CH_2-CH_2-CH_2$, $CH_2-S-S-CH_2$, $CH_2-CH_2-S-S-CH_2-CH_2$, $CH_2-O-CH_2$, $O-CH_2-CH_2-O$, $O-CH_2-CH_2-CH_2-O$, $O-CH_2-CH_2-CH_2-CH_2-O$, $O-CH_2-CH_2-O-CH_2-CH_2-O$, $O-CH_2-CH_2-O-CH_2-CH_2-O-CH_2-CH_2-O$, $O-CH_2-CH_2-SS-CH_2-CH_2-O$, $CO-CH_2-CH_2$, $O-CH_2-CH_2-CH_2-O-CO-CH_2-CH_2$, $O-CH_2-CH_2-CH_2-CH_2-CH_2-O-CO-CH_2-CH_2$, $O-CH_2-CH_2-CH_2-O-CH_2-CH_2-CH_2-O-CO-CH_2-CH_2$, $O-CH_2-CH_2-O-CO-CH_2-CH_2$, $NH-CH_2-CH_2-NH$, $NH-CH_2-CH_2-CH_2-NH$, $NH-CH_2-CH_2-CH_2-CH_2-NH$, $NH-CH_2-CH_2-CH_2-CH_2-CH_2-NH$, $NH-CH_2-CH_2-CH_2-CH_2-CH_2-CH_2-NH$, $O-CH_2-CH_2-S-S-CH_2-CH_2-O$ or $NH-CH_2-CH_2-S-S-CH_2-CH_2-NH$;

in the formula (1), Y is a substituent with the following structure:

$CH_2-O-\overset{\overset{O}{\|}}{P}(O^-)-O-CH_2CH_2-{}^+N(CH_3)_3$, $CH_2-O-\overset{\overset{O}{\|}}{P}(O^-)-O-CH_2CH_2-{}^+NH_3$, $CH_2-O-\overset{\overset{O}{\|}}{P}(O^-)-O-CH_2-CH(OH)-CH_2OH$, $CH_2-O-\overset{\overset{O}{\|}}{P}(O^-)-O-CH_2-CH({}^+NH_3)-COO^-$, $CH_2-{}^+NH_3$, ${}^+NH_3$, -continued $CH_2-{}^+NH_2(CH_3)-CH_3$, $CH_2-{}^+N(CH_3)_2-CH_3$

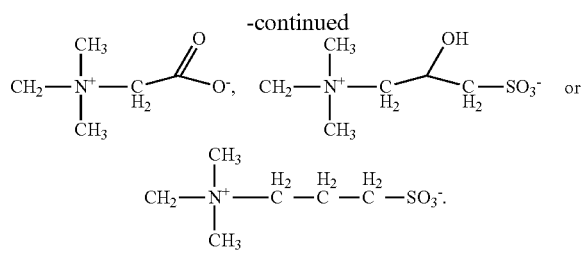

According to a pharmaceutical composition of the dihydroartemisinin dimer derivative of the present invention, the composition comprises the dihydroartemisinin dimer derivative, or the dihydroartemisinin dimer derivative and a pharmaceutically acceptable carrier.

According to a pharmaceutical composition of the dihydroartemisinin dimer derivative of the present invention, the composition comprises the dihydroartemisinin dimer derivative and a synergist, as well as a pharmaceutically acceptable carrier. The synergist may be one of the following substances:

benflumentol, amodiaquin, mefloquine, sulfadoxine, pyrimethamine, amodiaquine, chloroquine, tripiperaquine, ethyl hydrocupreine, primaquine, dichroine, halofantrine, quinine, floxacrine, amquinate, proguanil, amodiaquine, primaquine diphosphate, malaridine, chloroquine phosphate, naphthoquine phosphate, hydroxypiperquine, arteflene, hydroxypiperaquine phosphate, all-transretinoic acid, arsenous acid, ubenimex, dibromoducitol, arsenous acid, zorubicin, etoposide, corticotropin, carmustine, dexamethasone, cyclophosphamide, amsacrine, mercaptopurine, isoniazide, teniposide, fludarabine, aminocaproic acid, bucladesine, etoposide, corticotropin, dianhydrodulcitol for injection, levetiracetam, methotrexate, idarubicin, pirarubicin, adriamycin, ancitabine hydrochloride, nimustine, daunorubicin, mitoxantrone, epirubicin, aclarubicin, cytarabine, vincristine, hydroxy camptothecin, methylprednisolone, imatinib mesylate, ticlopidine, adriamycin, azathioprine, vinblastine sulfate, tioguanine, colchamine, vitamin A acid, hydroxyurea, amsacrine, etoposide, etoposide vepesid, cortisone acetate, dexamethasone, prednisone acetate, vinblastine injection, aclacinomycin A, razoxane, homoharringtonine, taxol, docetaxel, cabazitaxel, compound with code BAY59-8862, compound with code SB-T-11033, compound with code SB-T-121303, compound with code SB-T-121304, compound with code SB-T-1213, compound with code SB-T-12162, compound with code BMS-184476, compound with code DJ-927, compound with code BMS-275183, camptothecin, hydroxycamptothecin, 7-ethyl-10-hydroxycamptothecin, camptothecin-10-O-ethylpyrazole, irinotecan, topotecan, 7-t-butyldimethylsilyl-10-hydroxycamptothecin, camptothecin derivative with code Afeletecan, 7-hydroxymethyl camptothecin, 9-nitrocamptothecin, 9-aminocamptothecin, hexacyclic camptothecin, compound with code Gimatecan, compound with code Belotecan, diflomotecan, compound with code BN80927, compound with code TOP-0618, compound with code Exatecan, compound with code Lurtotecan, compound with code DRF-1042, podophyllotoxin, demethylepipodophyllotoxin, teniposide, etoposide, vinblastine, vincristine, vinorelbine, vindesine, etoposide, harringtonine, isoharringtonine, deoxyharringtonine, britannilactone, combretastatin, colchicine, fulvestrant, vorinostat, ixabepilone, eribulin, simvastatin, rotigotine, rifapentine, zidovudine, brivudin, lobucavir, megestrol, dibromidulcitol, salbutamol, resveratrol, homocamptothecin, aloeemodin, curcumin, lanosterol, cidofovir, aclarubicin, carubicin, zorubicin, 8-fluoro-idarubicin, nystatin, amphotericin, mitoxantrone, emodin, dactinomycin D, rapamycin, mithramycin, epothilone, mitomycin, bleomycin, fumagillol, methylprednisolone, flavopiridol, breviscapine, trabectedin, diterpenoids of euphorbiaceae species, 2,5-pentoxifylline, matrine, ixabepilone, combretastatin A4, ubenimex, ribavirin, marimastat, medroxyprogesterone, stavudine, saquinavir, phenylephrine, methoxamine, salbutamol, isoprenaline, misoprostol, latanoprost, epoprostenol, quinidine, propafenone, propranolol, digoxin, digitoxin, dobutamine, warfarin, coumarin compound, lovastatin, fluvastatin, empagliflozin, degarelix, abarelix, zoladex, galanthamine, actidione, minocycline, meloxicam, posaconazole, everolimus, vorinostat, vatalanib base, abiraterone, dihydroartemisinin, hydroprednisone, dexamethasone, compound with code Monomethyl auristatin E, bicalutamide, fenretinide, ansamycin, bryostatin, temsirolimus, prinomastat, tipranavir, indinavir, ritonavir, atazanavir, nelfinavir, batimastat, quercetin, flavonoid, ticagrelor, cangrelor, telbivudine, trifluridine, adapalene, lopinavir, dapagliflozin, rifaximin, fluticasone, isavuconazole, raltegravir, panobinostat, avibactam, levonorgestrel, ethinylestradiol, darunavir, olmesartan, ivacaftor, bryostatin-1, α-galactocerebrosides, epigallocatechin gallate, curcumin, oridonin, genistein, triptolide, gossypol, silibinin, telavancin, ezetimibe, pseudoephedrine, ticagrelor, mometasone furoate, deferiprone, oxybutynin, oxymorphone, raltegravir, mirabegron, teriflunomide, avanafil, temsirolimus, elvitegravir, dolutegravir, calicheamicin, retapamulin, tolvaptan, benflumentol, trabectedin, galanthamine, temsirolimus, canagliflozin, raltegravir, buprenorphine, sofosbuvir, treprostinil sodium, dantrolene, fluticasone furoate, naloxone, canagliflozin, sofosbuvir, N-hydroxymethyl aripiprazole, oxycodone, tacrolimus, paliperidone, N-hydroxymethyl aripiprazole, raltegravir, canagliflozin, dexamethasone, beleodaq, camptothecin derivative with code DX-8951f, gemcitabine, doxifluridine, cladribine, fluorouracil, tegafur, carmofur, tegadifur, doxifluridine, elacytarabine, capecitabine, 5'-deoxy-5-fluorocytidine, 5'-deoxy-5-fluorouridine, 2'-deoxy-5-fluorouridine, cytarabine, cyclocytidine, troxacitabine, sapacitabine, decitabine, bosutinib, tafetinib, ibrutinib, dacomitinib, neratinib, dovitinib, ponatinib, bafetinib, selumetinib, cabozantinib, ruxolitinib, alectinib, cabozantinib, lenvatinib, ceritinib, afatinib, sunitinib, lapatinib, crizotinib, apatinib, erlotinib, canertinib, axitinib, bosutinib, nilotinib, gefitinib, dasatinib, sitagliptin, imatinib, 6-mercaptopurin, methotrexate, aminopterinum, hydroxyurea, inosine dialdehyde, adenosine dialdehyde, ibrutinib, trametinib, ruxolitinib, azacitidine, clofarabine, lenalidomide, nelzarabine, pazopanib, vandetanib, carfilzomib, enzalutamide, dabrafenib, vatalanib, temozolomide, elvucitabine, betahistine, linagliptin, fluoxetine, alogliptin, vildagliptin, saxagliptin, duloxetine, atorvastatin, carmustine, nimustine, acadesine, 4'-thio-β-D-arabinofuranosylcytosine, adefovir, vidarabine, adriamycin, epirubicin, daunorubicin, idarubicin, pirarubicin, entinostat, chidamide, amdoxovir, lamivudine, entecavir, pixantrone, tacrine, lenalidomide, metisazone, hydroxyurea, pingyangmycin, ganciclovir, famciclovir, phentolamine, phenoxybenzamine, prazosin, tamsulosin, indoramin, brimonidine, hydralazine, minoxidil, mecamylamine, procainamide, mexiletine, dopamine, amrinone, palbociclib, boceprevir, telaprevir, huperzine-A, menantine, sorafenib, regorafenib, dabrafenib, vemurafenib, fingolimod, nintedanib, trifluridine, vonoprazan, olaparib, isophosphamide, eribulin, tipifarnib, lonafarnib, amprenavir, peptidomimetic drug, levetiracetam, eslicarbazepine, topiramate, vilazodone, imbruvica, doxazosin, oxcarbazepine, emtricitabine, adefovir dipivoxil, tenofovir, valganciclovir, milnacipran, aliskiren, ximelagatran, etravirine, rufinamide, imiquimod, famotidine, lamotrigine, boceprevir, ezogabine, colesevelam, imiquimod, chlortralidone, apixaban, abacavir, silodosin, degarelix, telavancin, fingolimod, sphingosine, riociguat, ombitasvir, cediranib, motesanib, palbociclib, rolapitan, dabigatran etexilate, desacetyl-vinblastine monohydrazide, MST-16, rilpivirine, cisplatin, spiroplatin, carboplatin, oxaliplatin, satraplatin, miriplatin, nedaplatin, sunplatinum, lobaplatin, cycloplatin, oxaliplatin, picoplatin, rhein, 9-cis retinoic acid, betulinic acid, vitamin E succinate, diclofenac, carglumic acid, obeticholic acid, deoxycholic acid, vigabatrin, leuprorelin, caerulein, pramlintide, adrenal cortical hormone, bacitracin, teriparatide acetate, goserelin, exenatide, mifamurtide, romidepsin, tyroservatide, sifuvirtide, albuvirtide, tyroserleutide, doripenem, azilsartan, oxytocin, cyclosporine, protirelin, taltirelin, nafarelin, buserelin, histrelin, gonadorelin, somatostatin, secretin, octreotide, ziconotide, enfuvirtide, lanreotide, vapreotide, seglitide, teduglutide, linaclotide, sinapultide, pasireotide, triptorelin, tesamorelin, liraglutide, bexarotene, pitavastatin, rosuvastatin, bendamustine, melphalan, lonidamine, atrasentan, melphalan, sulindac sulfone, pemetrexed, formylmerphalan, dinoprostone, carboprost, alprostadil, gemfibrozil, ciluprevir, pepstatin, glatiramer, lucinactant, indomethacin, ibuprofen, naproxen, deferasirox, fluoroquinolone, pralatrexate, tanomastat, marimastat, prinomastat, cilengitide, argatroban anhydrous, dabigatran, artesunate, ambrisentan, eltrombopag, valsartan, moxifloxacin, naproxen, eluxadoline, glatiramer, tirofiban, deferasirox, ceftazidime pentahydrate, levodopa, carbidopa, besivance, febuxostat, prulifloxacin, ceftobiprole medocaril, ceftobiprole, gabapentin enacarbil, mesalazine, icatibant, linaclotide, bedaquiline, sacubitril, brexpiprazole, doripenem, droxidopa, carubicin, aclarubicin, ibacitabine, galocitabine, ancitabine, lestaurtinib, improsulfan, mannosulfan, ritrosulfan, treosulfan, ecomustine, estramusting, semustine, alestramustine, gimeracil, medorubicin, pirarubicin, rodorubicin, valrubicin, zorubicin, leurubicin, idarubicin, galarubicin, esorubicin, detorubicin, amrubicin, valtorcitabine, zalcitabine, fiacitabine, flurocitabine, ambamustine, erlotinib, pelitinib, trimetrexate, edatrexate, ketotrexate, oteracil, mitoflaxone, bortezomib, beclomethasone dipropionate, mycophenolate mofetil, practolol, methylprednisolone, hydroxychloroquine sulfate, prednisone acetate, diflunisal, etodolac, betamethasone, diclofenac, indomethacin, dexamethasone, celecoxib, oxaprozin, nimesulide, ibuprofen, sodium tolmetin dihydrate, triamcinolone acetonide, leflunomide, flurbiprofen, flufenamic acid, hydrocortisone, hydroprednisone, clofenamic acid, aspirin, salicylic acid, loxoprofen, donepezil hydrochloride, benzydamine hydrochloride, meloxicam, sulindac, fenbufen, nabumetone, naproxen, aspirin-dl-lysine, ketoprofen, triamcinolone acetonide, hydrocortisone, fluticasone, clobetasol propionate, urotropine, ethacridine, levofloxacin, tacrolimus, tazarotene, clindamycin, metronidazole, clotrimazole, lidocaine, chlorhexidine, calcipotriene, nitrofurazone, imiquimod, miconazole, halcinonide, desonide, dithranol, indomethacin, neomycin, flumethasone, scopolamine, vitamin, diphenhydramine, ketoconazole, fluocinolone acetonide, cefaclor, cefdinir, butenafine, triamcinolone acetonide, lincomycin, fluorouracil, ofloxacin, chloramphenicol, thalidomide, methoxsalen, promethazine hydrochlorine, lomefloxacin, terbinafine, ciprofloxacin, cetirizine, cyproheptadine, netilmicin, sulfathiazole, erythromycin, vitamin B6, viaminate, bifonazole, benzyldodecyldimethylammonium bromide, diphenhydramine, zedoary oil, mupirocin, benzoyl peroxide, acrivastine, acyclovir, adapalene, and chloropheniramine maleate.

The pharmaceutical composition of the present invention is a liquid preparation, a solid preparation, a semi-solid preparation, a capsule, a granule, a gel, an injection, a sustained release preparation or a controlled release preparation.

The pharmaceutical composition of the present invention refers to nanoparticle with a particle size of 10 nm to 1000 nm.

According to an application of the dihydroartemisinin dimer derivative of the present invention and the pharmaceutical composition thereof in preparation of anti-parasitosis drugs, anti-autoimmune disease drugs, anti-tumor drugs, anti-leukemia drugs and skin disease drugs, the application is to prepare the dihydroartemisinin dimer derivative according to claim 1 or the pharmaceutically acceptable salt thereof into the pharmaceutical composition with the pharmaceutically acceptable carrier.

The dihydroartemisinin dimer derivative of the present invention and the pharmaceutical composition thereof are applied in preparation of drugs for treating or preventing malaria, schistosomiasis, toxoplasmosis, leishmaniasis, filariasis or ancylostomiasis.

The dihydroartemisinin dimer derivative of the present invention and the pharmaceutical composition thereof are applied in preparation of drugs for treating or preventing systemic lupus erythematosus, rheumatoid arthritis, systemic vasculitis, scleroderma, pemphigus, mixed connective tissue disease, autoimmune hemolytic anemia, thyroid autoimmune disease or ulcerative colitis.

The drugs for treating or preventing diseases caused by parasite, the drugs for treating autoimmune diseases and the anti-tumor drugs are pharmaceutical compositions prepared from the dihydroartemisinin dimer derivative above and the pharmaceutically acceptable carrier, or pharmaceutical compositions prepared from the dihydroartemisinin dimer derivative and the synergist, as well as the pharmaceutically acceptable carrier.

The drugs for treating or preventing malaria caused by plasmodium, the drugs for treating autoimmune diseases and the anti-tumor drugs are medicaments prepared from the pharmaceutical compositions prepared from the dihydroartemisinin dimer derivative above and the pharmaceutically acceptable carrier.

In a preferred solution of the pharmaceutical composition of the present invention, the pharmaceutical composition refers to liposomal nanoparticles with a particle size of 10 nm to 1000 nm, and the pharmaceutical composition also comprises an auxiliary agent. The auxiliary agent is preferably phospholipid and cholesterol.

In a preferred solution of the pharmaceutical composition of the present invention, the pharmaceutical composition refers to liposomal nanoparticles with a particle size of 10 nm to 1000 nm, and the liposome nanoparticles are loaded with a synergist.

The dihydroartemisinin dimer derivative of the present invention can exist in a form of isomer, comprising all possible stereoisomers and mixtures of two or more isomers.

The pharmaceutical composition of the compound of the present invention can be prepared according to a method commonly known in the art. For this purpose, if necessary, the compound of the present invention or the compound of the present invention combined with one or more solid or liquid pharmaceutical excipients and/or adjuvants can be prepared into an appropriate application form or dosage form for administration.

The compound of the present invention or the pharmaceutical composition containing the compound can be administered in unit dosage form, and an administration route can be an enteral route or a parenteral route, such as oral administration, intramuscular administration, subcutaneous administration, nasal administration, oral mucosa administration, skin administration, peritoneal administration or rectal administration.

The administration route of the compound of the present invention or the pharmaceutical composition containing the compound can be injection administration, comprising intravenous injection, intramuscular injection, subcutaneous injection, intradermal injection, acupoint injection, etc. An administration dosage form can be a liquid dosage form or a solid dosage form. For example, the liquid dosage form can be a true solution, a colloid, a microparticle dosage form, an emulsion dosage form and a suspension dosage form. Other dosage forms comprise tablet, capsule, dropping pill, aerosol, pill, powder, solution, suspension, emulsion, granule, suppository, lyophilized powder for injection, etc.

The compound of the present invention can be prepared into common preparation, and can also be prepared into slow release preparation, controlled release preparation, targeted preparation and various microparticle administration systems. In order to prepare the compound into various dosage forms, various carriers commonly known in the art can be widely used.

The compound of the present invention is prepared into injection preparation, such as solution, suspension solution, emulsion and freeze-dried powder injection, and the preparation can be aqueous or non-aqueous, and can contain one or more pharmaceutically acceptable carriers, diluents, adhesives, lubricants, preservatives, surfactants or dispersants. For example, the diluent can be selected from water, ethanol, polyethylene glycol, 1,3-propylene glycol, ethoxylated isostearyl alcohol, polyoxidized isostearyl alcohol, polyoxyethylene sorbitan fatty acid ester, phospholipid, etc.

Nanoparticles prepared from the compound of the present invention or the pharmaceutical composition containing the compound have a particle size of 10 nm to 1000 nm.

Liposome nanoparticles prepared from the compound of the present invention or the pharmaceutical composition containing the compound have a particle size of 10 nm to 1000 nm. Liposome nanoparticles prepared from the compound of the present invention and an auxiliary agent have a particle size of 10 nm to 1000 nm, and the auxiliary agent used is phospholipid. The auxiliary agent also contains a targeted group folic acid, a galactose, an antibody, a biotin or a polypeptide.

The liposomal nanoparticles of the pharmaceutical composition of the present invention are liquid preparation, solid preparation, semi-solid preparation, capsule, granule, gel, injection, sustained release preparation or controlled release preparation.

In terms of activity screening, the compound of the present invention or the composition shows a good plasmodium killing effect. The test shows that the compound of the present invention has no obvious in-vivo toxicity. Therefore, the compound can be used as anti-malaria drugs for animals, and is preferably used for mammals, especially human beings.

The compound of the present invention or the composition shows a good anti-tumor effect. The test shows that the compound of the present invention has no obvious in-vivo toxicity. Therefore, the compound can be used as anti-treatment drugs for human beings.

The compound of the present invention or the composition shows treatment to autoimmune diseases. The test shows that the compound of the present invention has no obvious in-vivo toxicity. Therefore, the compound can be used as drugs for treating autoimmune diseases for human beings.

The compound of the present invention or the composition shows treatment to systemic lupus erythematosus. The test shows that the compound of the present invention has no obvious in-vivo toxicity. Therefore, the compound can be used as drugs for treating systemic lupus erythematosus for human beings.

The compound of the present invention or the composition shows treatment to rheumatoid arthritis. The test shows that the compound of the present invention has no obvious in-vivo toxicity. Therefore, the compound can be used as drugs for treating rheumatoid arthritis for human beings.

A preparation method of the liposome nanoparticles of dihydroartemisinin dimer derivative of the present invention is that the liposome nanoparticles are prepared from a peroxide of the compound of the present invention or a mixture of the compound of the present invention and the auxiliary agent through methods such as a film dispersion method, a reverse phase evaporation method, a freeze drying method, an ultrasonic dispersion method, a spray drying method, a film extrusion method and a high-pressure homogenization method.

The dihydroartemisinin dimer derivative of the present invention contains two peroxy groups and anion, cation or zwitterion groups, with good hydrophilicity and water solubility; the peroxide is prepared into the nanoparticles according to the present invention, with a property of a liposome and a property of forming liquid preparation, solid preparation, semi-solid preparation, sterilization preparation and aseptic preparation; the dihydroartemisinin dimer derivative of the present invention and the pharmaceutical composition thereof are used for anti-malaria drugs, drugs for treating autoimmune diseases and drugs for treating tumors; and the dihydroartemisinin dimer derivative of the present invention and the pharmaceutical composition thereof have drug resistance without obvious toxic and side effects.

The dihydroartemisinin dimer derivative of the general formula (1) of the present invention and the pharmaceutical composition thereof are used for anti-malaria drugs, with good water solubility and an anti-malaria effect, and can overcome the defect of drug resistance of plasmodium caused by common artemisinin, that is, the dihydroartemisinin dimer derivative of the general formula (1) of the present invention and the pharmaceutical composition thereof are applied for anti-malaria drugs without causing drug resistance of parasite, and have good killing effect on artemisinin-resistant plasmodium.

The present invention is further described with reference to the following embodiments, but the present invention is not limited to the following embodiments.

Codes of some reagents used in the preparation process are as follows:

DMAP 4-dimethylaminopyridine; CDI N,N'-carbonyldiimidazole; DMSO dimethyl sulfoxide; GPC glycerophosphoryl choline; DBU 1,5-diazabicyclo[5.4.0]undec-5-ene; TEA triethylamine; DIEA N,N-diisopropylethylamine; and TFA trifluoroacetic acid.

Embodiment 1

Figure 2:
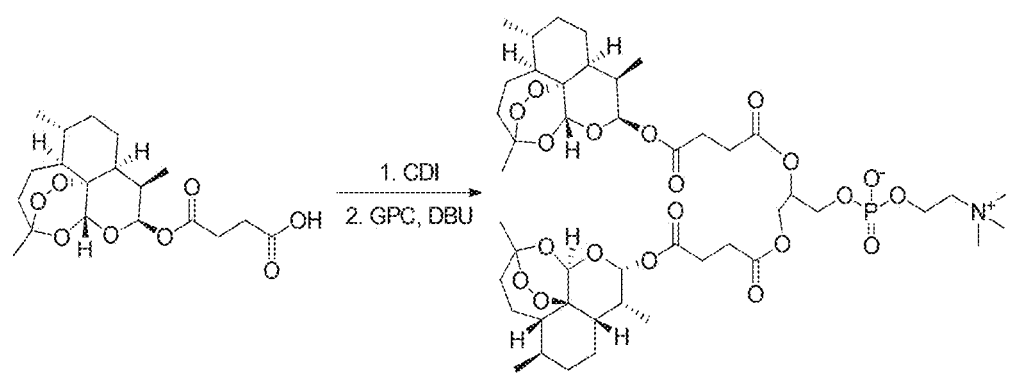
FIG. 2 illustrates a synthetic route of dihydroartemisinin dimer phosphatidylcholine.

Synthesis of Dihydroartemisinin Dimer Phosphatidylcholine (Referring to FIG. 2 for a Synthetic Route)

0.128 g of artesunate and 0.162 g of CDI were dissolved in 15 mL of dichloromethane, reacted at a room temperature for 4 h and dried in a rotary evaporation manner to remove the dichloromethane, then residuals were dissolved in 10 mL of dimethyl sulfoxide, added with 0.026 g of glycerophosphoryl choline and 0.05 g of DBU, and reacted overnight at 40° C. A product was purified by a flash chromatography system (chromatographic column: silica gel, and eluent: dichloromethane/methanol), the product was white solid with a yield of 35%, a purity of 97.3% that was detected by high performance liquid chromatography, and a 5 solubility of 16.96 g/L in water at 20° C. (an artesunate content was only 0.36 g/L). Mass Spectrum (MS) (m/z): $[M+Na]^+$ 1012.42. $^1$H-NMR (500 MHz, DMSO-$d_6$) refers to FIG. 3: δ 5.67 (d, J=8.3 Hz, 2H, H-10,10'), 5.55 (s, 2H, H-12,12'), 4.29-4.10 (m, 1H, H-20), 4.03-3.75 (m, 4H, H-21,22), 3.51-3.47 (m, 4H, H-23,24), 3.13 (s, 9H, H-25,26,27), 2.72-2.54 (m, 8H, H-18,18',17,17'), 2.42-1.29 (m, 24H, H-8a,8a',5a,5a',7,7',8,8',4,4',5,5',6,6',9,9'), 1.29 (s, 6H, H-13, 13'), 0.89 (d, J=6.2 Hz, 6H, H-15,15'), 0.77 (d, J=7.1 Hz, 6H, H-14,14'). $^{13}$C-NMR (500 MHz, CDCl$_3$): δ (ppm) 172.08, 171.79, 171.29, 171.21, 104.41, 92.26, 92.21, 91.43, 80.12, 70.85, 66.32, 62.92, 59.38, 54.36, 51.56, 45.19, 37.14, 36.21, 34.07, 31.78, 28.96, 28.90, 25.88, 24.55, 21.91, 20.17, 12.04.

Embodiment 2

Figure 3:
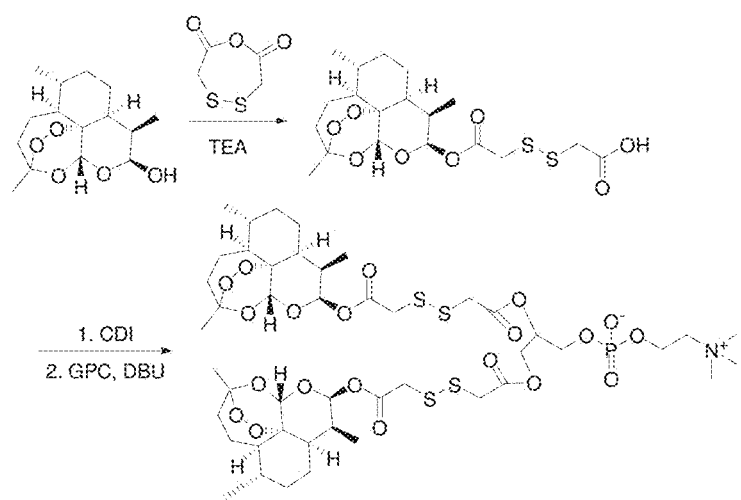
FIG. 3 illustrates a synthetic route of dihydroartemisinin dithiodiglycolic acid dimer phosphatidylcholine.

Synthesis of Dihydroartemisinin Dithiodiglycolic Acid Dimer Phosphatidylcholine (Referring to FIG. 3 for a Synthetic Route)

1.5 g of dihydroartemisinin and 1 g of dithiodianhydride were dissolved in 20 mL of chloroform, added with 0.5 g of triethylamine, and stirred and reacted overnight at 40° C. The solvent was removed, separation and purification were performed by a flash chromatography system (chromatographic column: silica gel, and eluent: dichloromethane/methanol), and obtained a product was 1.8 g of white solid of dihydroartemisinin dithiodiglycolic acid.

0.5 g of white solids of dihydroartemisinin dithiodiglycolic acid and 0.3 g of CDI were dissolved in 15 mL of dichloromethane, reacted at a room temperature for 3 h and dried in a rotary evaporation manner to remove the dichloromethane, then residuals were dissolved in 10 mL of dimethyl sulfoxide, added with 0.12 g of glycerophosphoryl choline and 0.3 g of DBU, and reacted overnight at 40° C. Product was purified by a flash chromatography system (chromatographic column: silica gel, and eluent: chloroform/methanol), an obtained product was white solid of dihydroartemisinin dithiodiglycolic acid dimer phosphatidylcholine with a yield of 30%, a purity of 95% that was detected by high performance liquid chromatography, and a solubility of 13.6 g/L in water.

Mass spectrum analysis (m/z): $[M+H]^+$ 1119.29.

Embodiment 3

Figure 4:
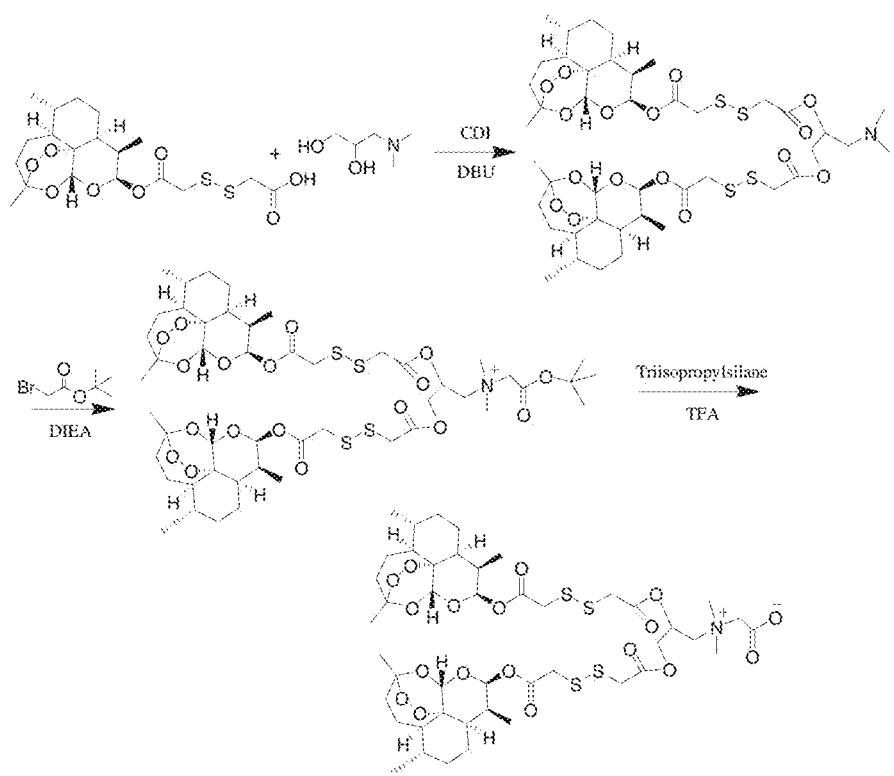
FIG. 4 illustrates a synthetic route of dihydroartemisinin dithiodiglycolic acid dimer carboxyl betaine.

Synthesis of Dihydroartemisinin Dithiodiglycolic Acid Dimer Carboxyl Betaine (Referring to FIG. 4 for a Synthetic Route)

0.3 g of the dihydroartemisinin dithiodiglycolic acid of Embodiment 10 and 0.2 g of CDI were dissolved in 10 mL of dichloromethane, reacted at a room temperature for 2 h and dried in a rotary evaporation manner to remove the dichloromethane, then residuals were dissolved in 10 mL of dimethyl sulfoxide, added with 0.1 g of 3-dimethylamino-1,2-propanediol and 0.2 g of DBU, and reacted overnight at 35° C. Product was purified by a flash chromatography system (chromatographic column: silica gel, and eluent: chloroform/methanol), obtained product A was 0.24 g of white solid of dihydroartemisinin dithiodiacetate dimer-1 and 2-propanediol N,N-dimethylamino.

0.12 g of product A was dissolved in 20 mL of dichloromethane, added with 0.1 g of DIEA, and stirred at 25° C. for 20 min, and then 0.2 g of tert-butyl bromoacetate was slowly added into a reaction system, and heated to 55° C. and reacted for 24 h. A reaction solution was diluted to 50 mL with dichloromethane, washed three times with 1 M hydrochloric acid, and dried with Na$_2$SO$_4$, and a solvent was evaporated by rotation to obtain 0.1 g of products B.

0.1 g of product B was dissolved in 20 mL of dichloromethane, added with 10 ml of TFA and 1 mL of triisopropylsilane, and reacted at 25° C. for 2 h. A reaction solution was diluted to 50 mL with dichloromethane, washed three times with saturated NaHCO$_3$, and dried with Na$_2$SO$_4$, and a solvent was evaporated by rotation to obtain crude products. The crude product was purified by silica gel column (a mobile phase was dichloromethane: methanol/65:25) to obtain product of dihydroartemisinin dithiodiglycolic acid dimer carboxyl betaine. The product was 0.08 g of white powder with a product purity of 96.6% and a solubility of 15.3 g/L in water. MS: $[M+H]^+$ 1039.27.

Embodiment 4

Figure 5:
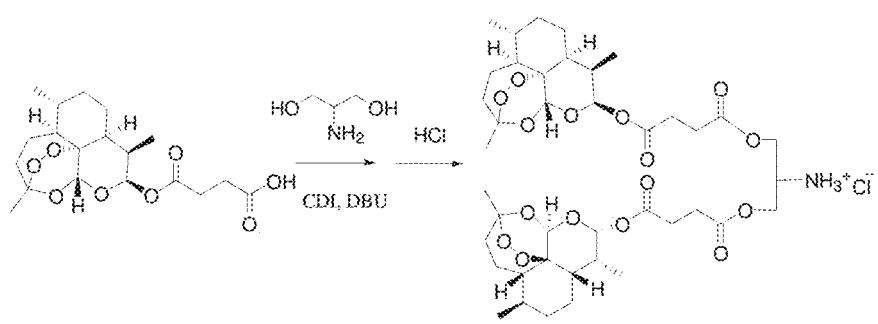
FIG. 5 illustrates a synthetic route of dihydroartemisinin dimer serinol hydrochloride.

Synthesis of Dihydroartemisinin Dimer Serinol Hydrochloride (Referring to FIG. 5 for a Synthetic Route)

0.1 g of artesunate and 0.1 g of CDI were dissolved in 15 mL of dichloromethane, reacted at a room temperature for 4 h and dried in a rotary evaporation manner to remove the dichloromethane, then residuals were dissolved in 10 mL of dimethyl sulfoxide, added with 0.06 g of serinol and 0.1 g of DBU, and reacted overnight at 40° C., with pH adjusted with hydrochloric acid as 6. Product was purified by a flash chromatography system (chromatographic column: silica gel, and eluent: dichloromethane/methanol), the product was white solid of dihydroartemisinin dimer serinol hydrochloride with a yield of 65% and a purity of 98.3% that was detected by high performance liquid chromatography. Mass spectrum (m/z): $[M+Na]^+$1012.42.

Embodiment 5

Figure 6:
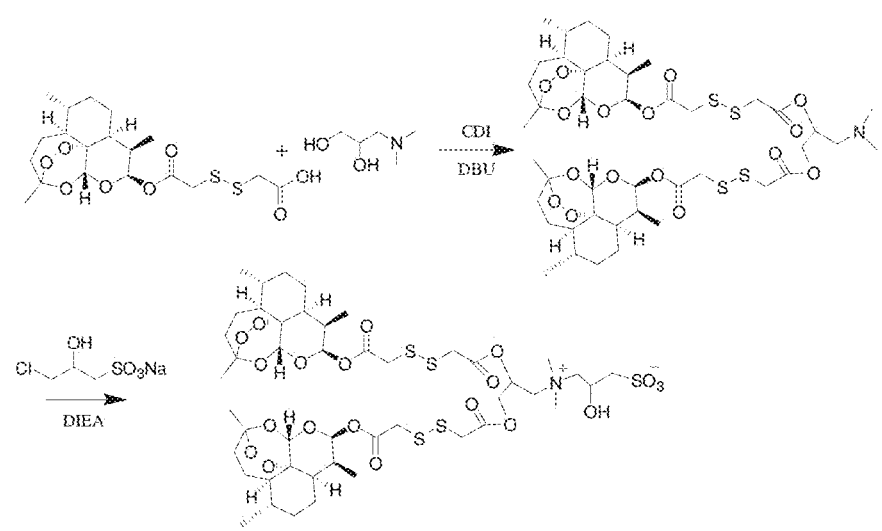
FIG. 6 illustrates a synthetic route of dihydroartemisinin dithiodiglycolic acid dimer hydroxysulfobetaine.

Synthesis of Dihydroartemisinin Dithiodiglycolic Acid Dimer Hydroxysulfobetaine (Referring to FIG. 6 for a Synthetic Route)

0.12 g of the products A of dihydroartemisinin dithiodiacetate dimer-1 and 2-propanediol N,N-dimethylamino of Embodiment 11 were dissolved in 20 mL of dichloromethane, added with 0.1 g of DIEA, and stirred at 25° C. for 20 min, and then 0.3 g of 3-chloro-2-hydroxypropanesulfonic acid sodium was slowly added into a reaction system, and heated to 55° C. and reacted for 24 h. The reaction solution was diluted to 50 mL with dichloromethane, washed three times with 1 M hydrochloric acid, and dried with Na$_2$SO$_4$, and a solvent was evaporated by rotation to obtain crude product. The crude product was purified by silica gel column (a mobile phase was dichloromethane:methanol/50:50) to obtain product of dihydroartemisinin dithiodiglycolic acid

Embodiment 6

Figure 7:
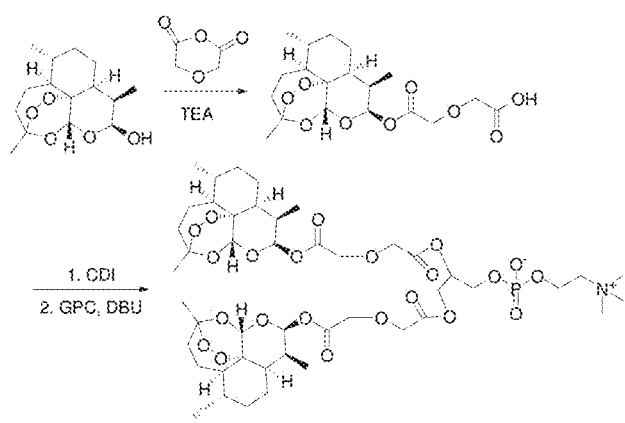
FIG. 7 illustrates a synthetic route of dihydroartemisinin diglycolic acid dimer phosphatidylcholine.

Synthesis of Dihydroartemisinin Diglycolic Acid Dimer Phosphatidylcholine (Referring to FIG. 7 for a Synthetic Route)

1 g of dihydroartemisinin and 1 g of diglycolic anhydride were dissolved in 20 mL of chloroform, added with 1 g of triethylamine, and stirred and reacted at 40° C. overnight. A solvent was removed, separation and purification were performed by a flash chromatography system (chromatographic column: silica gel, and eluent: dichloromethane/methanol), and obtained product was 1.1 g of white solid of dihydroartemisinin diglycolic acid.

1 g of white solid of dihydroartemisinin diglycolic acid and 0.6 g of CDI were dissolved in 15 mL of dichloromethane, reacted at a room temperature for 3 h and dried in a spinning manner to remove the dichloromethane, then residuals were dissolved in 10 mL of dimethyl sulfoxide, added with 0.3 g of glycerophosphoryl choline and 0.6 g of DBU, and reacted overnight at 40° C. Product was purified by a flash chromatography system (chromatographic column: silica gel, and eluent: chloroform/methanol), obtained product was white solid of dihydroartemisinin diglycolic acid dimer phosphatidylcholine with a yield of 56% and a purity of 96.5% that was detected by high performance liquid chromatography.

Mass spectrum analysis (m/z): $[M+H]^+$ 1023.03.

Embodiment 7

Figure 8:
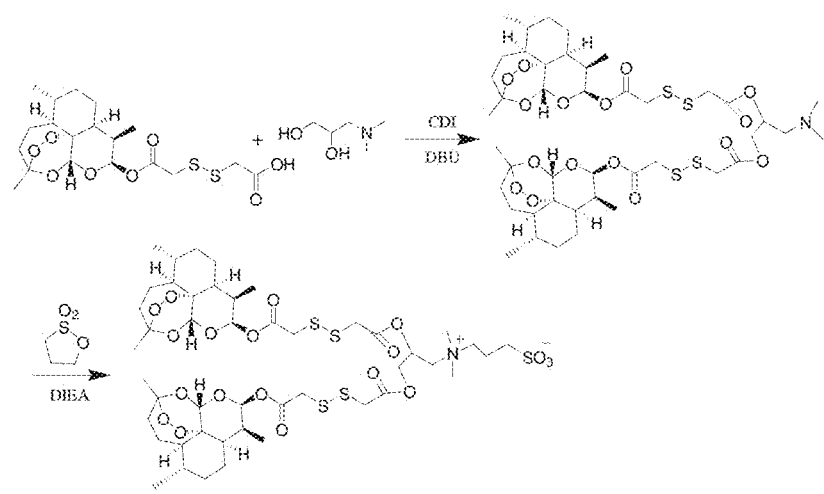
FIG. 8 illustrates a synthetic route of dihydroartemisinin dithiodiglycolic acid dimer sulfobetaine.

Synthesis of Dihydroartemisinin Dithiodiglycolic Acid Dimer Sulfobetaine (Referring to FIG. 8 for a Synthetic Route)

0.1 g of the product A of dihydroartemisinin dithiodiacetate dimer-1 and 2-propanediol N,N-dimethylamino of Embodiment 11 were dissolved in 20 mL of dichloromethane, added with 0.1 g of DIEA, and stirred at 25° C. for 20 min, and then 0.3 g of propanesultone was slowly added into a reaction system, and heated to 55° C. and reacted for 24 h. The reaction solution was diluted to 50 mL with dichloromethane, washed three times with 1 M hydrochloric acid, and dried with $Na_2SO_4$, and the solvent was evaporated by rotation to obtain crude product. The crude product was purified by silica gel column (a mobile phase was dichloromethane:methanol/50:50) to obtain product of dihydroartemisinin dithiodiglycolic acid dimer sulfobetaine. The product was 0.07 g of white powder with a product purity of 98.2%. MS: $[M+H]^+$ 1103.37.

Embodiment 8

Figure 9:
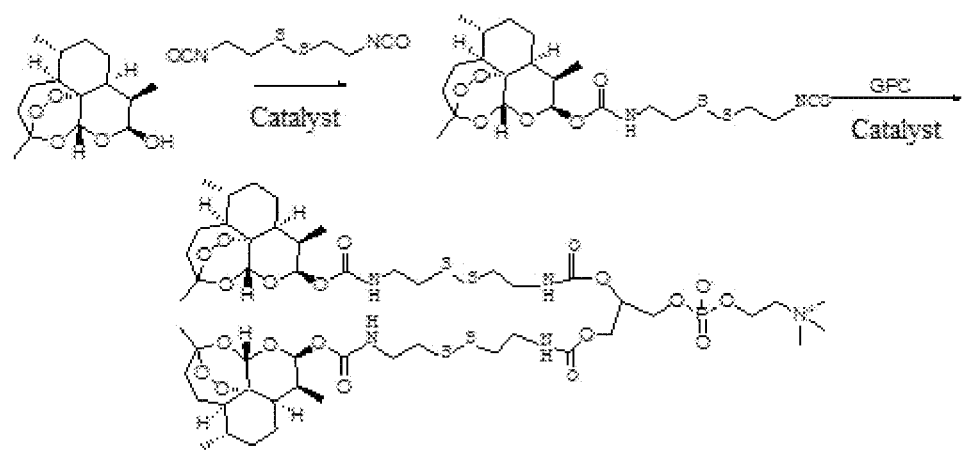
FIG. 9 illustrates a synthetic route of dihydroartemisinin diethyldithiocarbamate acid ester dimer phosphatidylcholine.

Synthesis of Dihydroartemisinin Diethyldithiocarbamate Acid Ester Dimer Phosphatidylcholine (Referring to FIG. 9 for a Synthetic Route)

1 g of dihydroartemisinin and 0.4 g of dithiodiethyl diisocyanate were dissolved in 20 mL of chloroform, added with 0.1 g of dibutyltin dilaurate, and stirred and reacted at 40° C. for 6 h. 0.3 g of glycerophosphoryl choline was added, and continued to react at 40° C. for 10 h. The solvent was removed, and separation and purification were performed by a flash chromatography system (chromatographic column: silica gel, and eluent: dichloromethane/methanol), and obtained product was 1.2 g of white solid of dihydroartemisinin diethyldithiocarbamate acid ester dimer phosphatidylcholine. Mass spectrum analysis (m/z): $[M+H]^+$ 1235.45.

Embodiment 9

Figure 10:
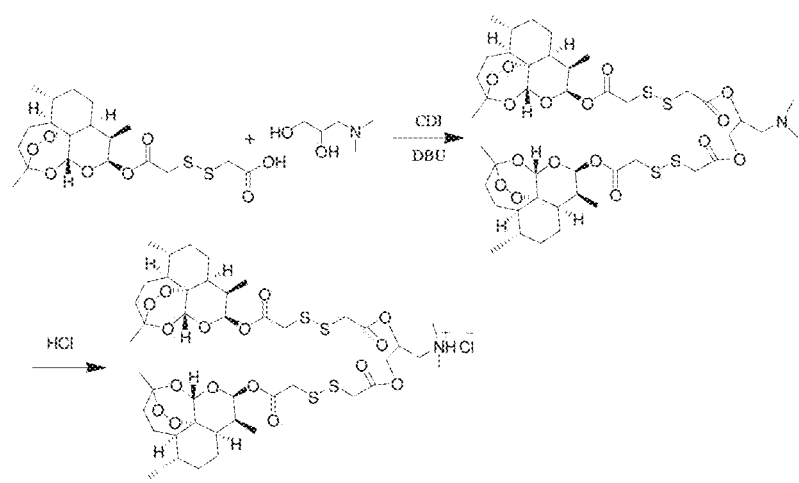
FIG. 10 illustrates a synthetic route of dihydroartemisinin dithiodiglycolic acid dimer—N,N-dimethylamino hydrochloride.

Synthesis of Dihydroartemisinin Dithiodiglycolic Acid Dimer-N,N-Dimethylamino Hydrochloride (Referring to FIG. 10 for a Synthetic Route)

0.1 g of the product A of dihydroartemisinin dithiodiacetate dimer-1 and 2-propanediol N,N-dimethylamino of Embodiment 11 were added with hydrochloric acid for acidification to obtain crude product. The crude product was purified by silica gel column (a mobile phase was dichloromethane:methanol/50:50) to obtain product of dihydroartemisinin dithiodiglycolic acid dimer-N,N-dimethylamino hydrochloride. The product was 0.06 g of white powder with a product purity of 96.2%. MS (m/z): $[M+H]^+$ 1017.23.

Embodiment 10

Figure 11:
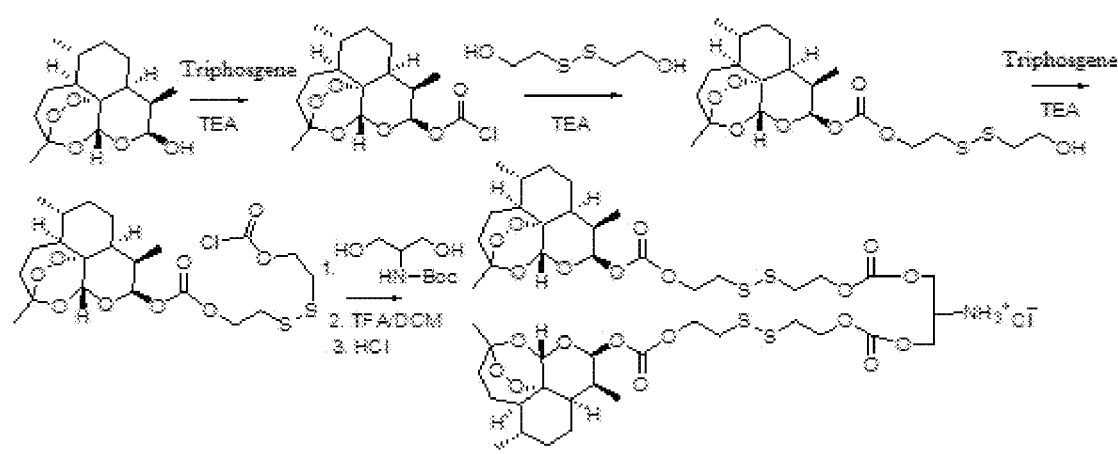
FIG. 11 illustrates a synthetic route of dihydroartemisinin dithiodiglycol carbonic ester dimer serinol hydrochloride.

Synthesis of Dihydroartemisinin Dithiodiglycol Carbonic Ester Dimer Serinol Hydrochloride (Referring to FIG. 11 for a Synthetic Route)

1 g of dihydroartemisinin was dissolved in 20 mL of chloroform, added with 1 g of triethylamine and 0.4 g of triphosgene, and stirred and reacted at 40° C. for 1 h. The solvent was removed, and 0.3 g of dithiodiethylene glycol was added, and reacted for 3 h. The solvent was removed, separation and purification were performed on crude products by a flash chromatography system (chromatographic column: silica gel, and eluent: dichloromethane/methanol), and an obtained product was 0.7 g of dihydroartemisinin dithiodiglycol. An intermediate product was dissolved in 10 mL of dichloromethane, added with 1 g of triethylamine and 0.3 g of triphosgene, and stirred and reacted at 40° C. for 1 h, then 0.3 g of serinol protected by tert-butoxycarbonyl was added, and after the reaction was completed, a protecting group was removed with trifluoroacetic acid and treated with hydrochloric acid. The product was purified by a flash chromatography system (chromatographic column: silica gel, and eluent: chloroform/methanol), and obtained products were white solid of dihydroartemisinin dithiodiglycol carbonic ester dimer serinol hydrochloride with a yield of 35% and a purity of 95.3% that was detected by high performance liquid chromatography. Mass spectrum analysis (m/z): $[M+H]^+$ 1109.40.

Embodiment 11

Figure 12:
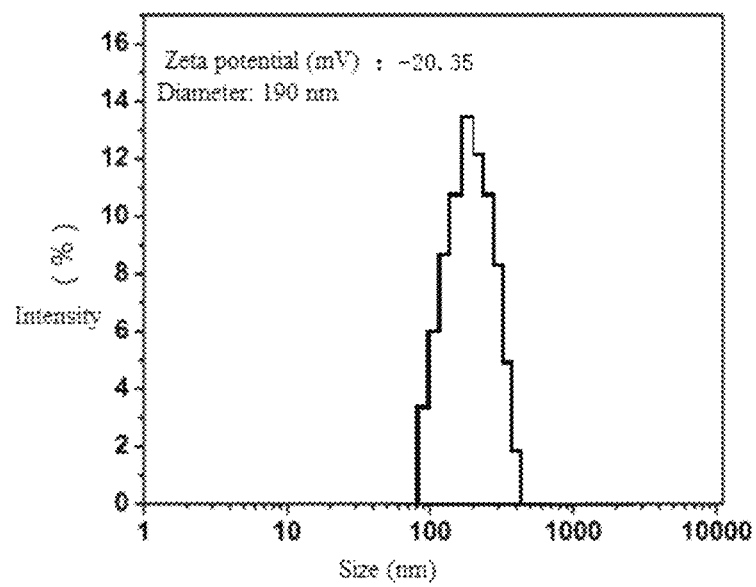
FIG. 12 illustrates dynamic light scattering particle size analysis of a liposome of dihydroartemisinin dimer phosphatidylcholine.
Figure 13:
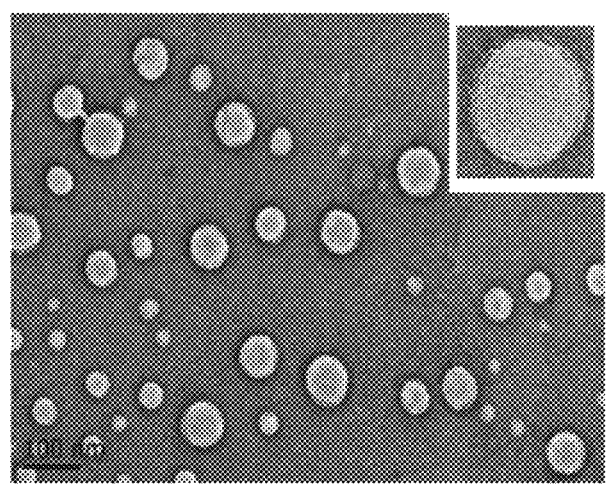
FIG. 13 illustrates a transmission electron microscopy image of liposomal nanoparticles of dihydroartemisinin dimer phosphatidylcholine.

Preparation of a Liposome of Dihydroartemisinin Dimer Phosphatidylcholine by a Thin Film Method 10 mg of the dihydroartemisinin dimer phosphatidylcholine of Embodiment 1 was dissolved in 10 ml of methanol, a solvent was removed by rotary evaporation, and then 10 ml of PBS buffer (pH 7.4) was added and shaken at 50° C. for 10 min. Finally, the mixture was filtered with a filter membrane of 0.22 micron to obtain a liposome nanoparticles solution of dihydroartemisinin dimer phosphatidylcholine. Particle size analysis results (Autosizer 4700 Malvern Dynamic Light Scattering Instrument) are shown in FIG. 12 below, wherein an average particle size was 190 nm and a Zeta potential was −20.35 mV. FIG. 13 shows a morphology of the nanoparticles measured by a transmission electron microscope (200 kV, JEM-2100 system, JEOL), which shows a double lipid layer structure of the liposome.

Embodiment 12

Preparation of a Long-Circulation Liposome of Dihydroartemisinin Dimer Phosphatidylcholine by a Thin Film Method 20 mg of the dihydroartemisinin dimer phosphatidylcholine of Embodiment 1 and 6 mg of distearoyl phosphoethanolamine-polyethylene glycol (DSPE-PEG, wherein a molecular weight of PEG was 2000) were dissolved in 20 ml of chloroform. The solvent was removed by rotary evaporation, and then 20 ml of PBS buffer (pH 7.4) was added and shaken at 50° C. for 10 min. Finally, the mixture was filtered with a filter membrane of 0.22 micron to obtain a long-circulation liposome nanoparticle solution of dihydroartemisinin dimer phosphatidylcholine. The particle size analysis showed that an average particle size was 150 nm. Freeze drying was performed on the liposome nanoparticle solution to obtain powder nanoparticles.

Embodiment 13

Preparation of a Co-Assembled Liposome of Dihydroartemisinin Dimer Phosphatidylcholine by a Thin Film Method 10 mg of the dihydroartemisinin dimer phosphatidylcholine of Embodiment 1 and 10 mg of distearoyl phosphatidylcholine were dissolved in 20 ml of methanol. The solvent was removed by rotary evaporation, and then 20 ml of PBS buffer (pH 7.4) was added and shaken at 50° C. for 10 min. Finally, the mixture was filtered with a filter membrane of 0.22 micron to obtain a co-assembled liposome nanoparticles solution of dihydroartemisinin dimer phosphatidylcholine. A particle size analysis result was that an average particle size was 185 nm. Freeze drying was performed on the liposome nanoparticles solution to obtain powder nanoparticles.

Embodiment 14

Preparation of a Liposome of Dihydroartemisinin Dithiodiglycolic Acid Dimer Phosphatidylcholine by a Thin Film Method 10 mg of the dihydroartemisinin dithiodiglycolic acid dimer phosphatidylcholine of Embodiment 2 was dissolved in 10 ml of methanol. The solvent was removed by rotary evaporation, and then 10 ml of PBS buffer (pH 7.4) was added and shaken at 50° C. for 10 min. Finally, the mixture was filtered with a filter membrane of 0.22 micron to obtain a liposome nanoparticle solution of dihydroartemisinin dithiodiglycolic acid dimer phosphatidylcholine. The particle size analysis showed that an average particle size was 170 nm. Freeze drying was performed on the liposome nanoparticle solution to obtain powder nanoparticles.

Embodiment 15

Preparation of Nanoparticles of Dihydroartemisinin Dithiodiglycolic Acid Dimer Carboxyl Betaine by a Thin Film Method 10 mg of the dihydroartemisinin dithiodiglycolic acid dimer carboxyl betaine of Embodiment 3 was dissolved in 10 ml of methanol, a solvent was removed by rotary evaporation, and then 10 ml of PBS buffer (pH 7.4) was added and shaken at 50° C. for 10 min. Finally, the mixture was filtered with a filter membrane of 0.22 micron to obtain a nanoparticle solution of dihydroartemisinin dithiodiglycolic acid dimer carboxyl betaine. The particle size analysis showed that an average particle size was 190 nm. Freeze drying was performed to obtain powder nanoparticles.

Experiment 16

Pharmacokinetics of a Liposome of Dihydroartemisinin Dimer Phosphatidylcholine

BALB/c mice (female, five weeks, 20 g to 22 g) were divided into four groups (three mice in each group). Artesunate was used for the first group; the dihydroartemisinin dimer phosphatidylcholine of Embodiment 1 was used for the second group; the liposome of dihydroartemisinin dimer phosphatidylcholine of Embodiment 11 was used for the third group; and the long-circulation liposome of dihydroartemisinin dimer phosphatidylcholine of Embodiment 12 was used for the fourth group (an administration dosage of the artesunate was 10 mg/kg, referring to equivalent artesunate molar dosage). A PBS solution of drugs was injected through tail vein.

Blood samples were respectively taken at predetermined times (0.25 h, 0.5 h, 1 h, 3 h, 6 h, 12 h, 24 h and 48 h) and centrifuged at 3,000 rpm for 10 min to obtain plasma. Drugs in blood were extracted with methanol, and analyzed and measured by HPLC (Agilent 1100, CA) (HPLC analysis, artesunate eluent: acetonitrile/water=51/49, containing 0.1% TFA; dihydroartemisinin dimer phosphatidylcholine eluent: acetonitrile/water=60/40, containing 0.1% TFA; flow rate: 1.0 mL/min; temperature: 25° C., and measurement wavelength: 210 nm), and a drug concentration in blood and kinetic parameters were calculated.

Figure 14:
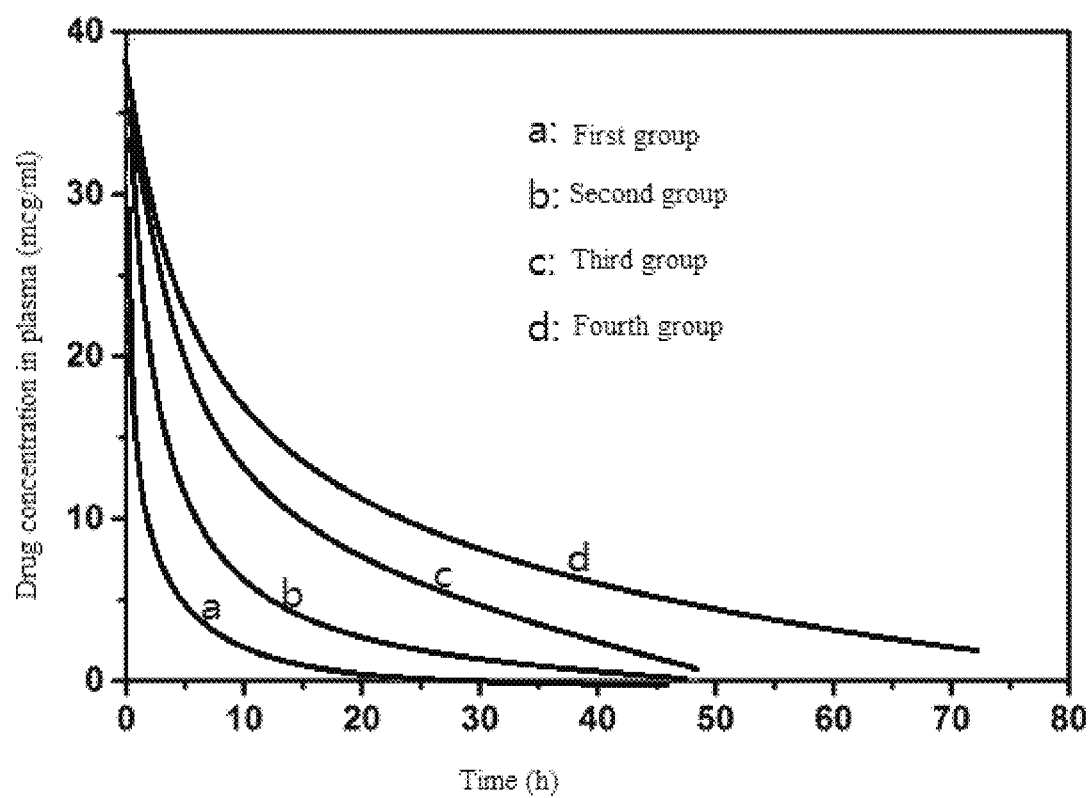
FIG. 14 illustrates a relationship between a drug concentration in blood and a time after administration of different drugs.

Result: the relationship between the drug concentration in blood and the time is shown in FIG. 14, and the calculated pharmacokinetic parameters are shown in Table 1.

It can be seen that the metabolism of artesunate in blood is basically completed within 3 h to 4 h, a half-life of the dihydroartemisinin dimer phosphatidylcholine is higher than that of parent drug, reaching more than 9 h, while a blood clearance half-life of the liposome of dihydroartemisinin dimer phosphatidylcholine is as long as 13 h, and a maximum drug concentration reaches 34.68 μg/mL, which is higher than 23.4 μg/mL of the artesunate. In addition, a bioavailability of the liposome of dihydroartemisinin dimer phosphatidylcholine is more than six times that of the artesunate, while a plasma clearance rate $C_L$(0.019 L/h/kg) is far lower than a value of the artesunate. A drug blood clearance half-life of the long-circulation liposome is more than 20 h, which shows a prominent long-term effect of drugs and a higher bioavailability of drugs. Therefore, the liposome of dihydroartemisinin dimer phosphatidylcholine has a very long blood circulation time and a very low plasma clearance rate.

TABLE 1

Pharmacokinetic Parameters of Liposome of Dihydroartemisinin Dimer Phosphatidylcholine (Intravenous Administration)

| Parameter (unit)* | First group | Second group | Third group | Fourth group |
|---|---|---|---|---|
| $AUC_{0-t}$ (μg · h/mL) | 80.685 | 285.975 | 519.610 | 689.553 |
| $MRT_{0-t}$ (h) | 2.714 | 13.833 | 19.075 | 29.929 |
| K | 0.345 | 0.072 | 0.052 | 0.033 |
| $t_{1/2}$ (h) | 1.517 | 9.587 | 13.219 | 20.741 |
| $C_L$ (L/h/kg) | 0.224 | 0.035 | 0.019 | 0.015 |
| $V_d$ (L/kg) | 0.756 | 0.484 | 0.367 | 0.434 |
| $C_{max}$ (μg/mL) | 23.4 | 34.48 | 34.68 | 37.74 |

*Parameters: AUC, area under the curve 0-t; $MRT_{0-t}$, residence time; K, elimination rate constant; $t_{1/2}$, elimination half-life; $C_L$, plasma clearance rate; $V_d$, apparent distribution volume; and $C_{max}$, plasma peak concentration.

Embodiment 17

In-vitro degradation test of a liposome of dihydroartemisinin dimer phosphatidylcholine Sample: the dihydroartemisinin dimer phosphatidylcholine prepared in Embodiment 1 was dissolved in 5 mL of PBS (pH 7.4) solution, PBS (pH 7.4, containing 10% fetal bovine serum FBS) solution and PBS (pH 5.0) solution to prepare a solution with a concentration of 0.1 mg/mL; and the liposome nanoparticle solution of dihydroartemisinin dimer phosphatidylcholine prepared in Embodiment 11 was respectively diluted with 5 mL of PBS (pH 7.4), PBS (pH 7.4, containing 10% FBS) and PBS (pH 5.0) to a concentration of 0.1 mg/mL. Incubation was performed at 37° C. for 24 h. At a predetermined time (0.5 h, 1 h, 3 h, 5 h, 10 h, 15 h, 20 h and 24 h), 20 μl of sample solution was taken, and a content of the dihydroartemisinin dimer phosphatidylcholine was measured by the HPLC method. (Agilent 1100 Chromatographic Instrument, Zorbax Reversed Phase C18 Column, 150×4.6 mm, 5 μm, sample size 20 μL, column temperature 25° C., and detection wavelength $\lambda=254$ nm; and gradient elution: 2% to 90% buffer B/A, flow rate 1.0 mL/min, buffer A: deionized water of 0.1% TFA, and buffer B: acetonitrile of 0.1% TFA).

Figure 15:
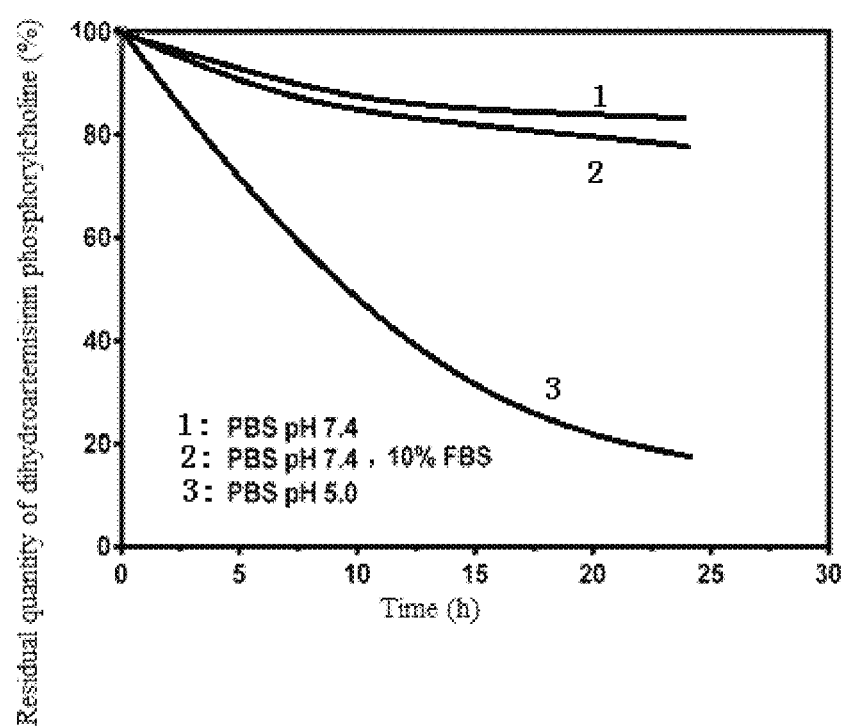
FIG. 15 illustrates a relationship between a content of dihydroartemisinin dimer phosphatidylcholine and a time after in-vitro degradation of the liposome of dihydroartemisinin dimer phosphatidylcholine.

Result: a relationship between the content of the dihydroartemisinin dimer phosphatidylcholine and the time is shown in FIG. 15. The result shows that the content of the dihydroartemisinin dimer phosphatidylcholine is as high as 80% after 24 h at pH 7.4 (without or with FBS), which indicates that the in-vitro degradation of the liposome of dihydroartemisinin dimer phosphatidylcholine is very slow, and also indicates that the liposome is relatively stable under a simulated physiological condition. Under a condition of pH 5.0, the in-vitro degradation of the liposome of dihydroartemisinin dimer phosphatidylcholine is very fast, and a degradation rate of the dihydroartemisinin dimer phosphatidylcholine reaches 88% after 24 h. Therefore, the liposome of dihydroartemisinin dimer phosphatidylcholine is easy to be disintegrated and degraded under an acidic condition.

Embodiment 18

In-Vitro Drug Release Test of a Liposome of Dihydroartemisinin Dimer Phosphatidylcholine 10 mL of the liposome solution of dihydroartemisinin dimer phosphatidylcholine of Embodiment 11 (concentration: 1 mg/mL) was placed in a dialysis bag (MWCO 1000). The dialysis bag was immersed in 200 mL of PBS (pH 7.4) buffer, PBS (pH 7.4, containing 10% fetal bovine serum FBS) buffer and PBS (pH 5.0) buffer (adding 0.5% Tween 80 at the same time) and incubated in an incubator at 37° C. 10 mL of dialysate was sampled at a predetermined time (0.5 h, 1 h, 3 h, 5 h, 10 h, 15 h, 20 h and 24 h) and added with an equal volume of new buffer. The dialysate was dissolved in 2 mL of methanol after freeze drying and analyzed by high performance liquid chromatography.

Figure 16:
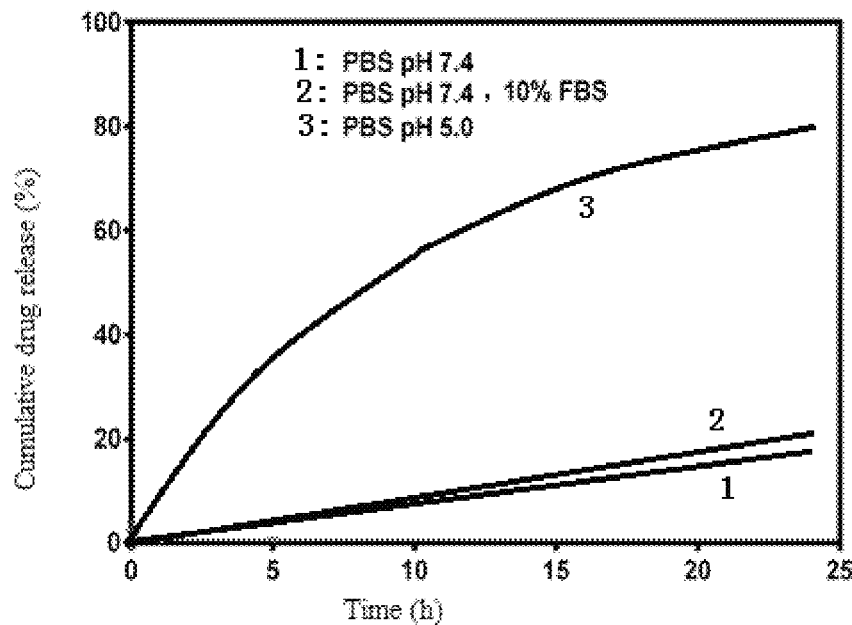
FIG. 16 illustrates a relationship between a content of artesunate released and a time after in-vitro degradation of the liposome of dihydroartemisinin dimer phosphatidylcholine.

Result: a content of artesunate released after liposome degradation is shown in FIG. 16. Obviously, under a neutral condition, the artesunate released within 24 h is less than 20%. Under an acidic condition, 85% of artesunate is released.

Embodiment 19

Cellular Uptake Test of a Liposome of Dihydroartemisinin Dimer Phosphatidylcholine Laser scanning confocal microscopy: a MCF-7 cell ($2.0\times10^5$) was planted in each well of a culture plate, added with a liposome of dihydroartemisinin dimer phosphatidylcholine (50 μg/mL) loaded with a fluorescence probe Cy 5.5, and incubated for 3 h. Under the same condition, the same amount of Cy 5.5 was used as a control group (containing the same amount of artesunate). Then, a culture solution was removed, and the cell was washed twice with PBS, and fixed with 4% formaldehyde solution for 30 min (25° C.). Finally, the cell was processed with 100 μL (10 μg/mL) of 4',6-diamidino-2-phenylindole (DAPI) solution for 5 min, and washed three times with PBS. The cell was observed with Leica TCS SP8 laser scanning confocal microscope (Leica, Germany).

Result: no fluorescence is observed in the control group after 3 h, while the cell processed with the liposome of dihydroartemisinin dimer phosphatidylcholine shows a strong fluorescence intensity, which indicates that the liposome of dihydroartemisinin dimer phosphatidylcholine is rapidly uptaken by the MCF-7 cell.

Embodiment 20

Intracellular Degradation Test of a Liposome of Dihydroartemisinin Dimer Phosphatidylcholine A MCF-7 cell ($1.0\times10^5$) was planted in each well of a culture plate with six wells, with a DMEM medium, and incubated for 24 h. Then, a culture solution was removed and the cell was washed with PBS. The liposome of dihydroartemisinin dimer phosphatidylcholine of Embodiment 11 (100 μg/mL) was added and continuously cultured at 37° C. for 12 h. The medium was carefully removed, and 5 mL of mixed solution of methanol and PBS (volume ratio 1:1) was added to extract and centrifuge. An extract of a supernatant was analyzed by a mass spectrometer after freeze drying.

Result: in the cell extract, a molecular ion peak of artesunate is found to be 385.6 (M+H+, m/z) through the mass spectrometry analysis, which indicates that the liposome of dihydroartemisinin dimer phosphatidylcholine is internalized by the cell and degraded in the cell to release original drug of artesunate.

Experiment Example 21

Preparation of a Liposome of Dihydroartemisinin Dimer Phosphatidylcholine Loaded with Mefloquine by a Thin Film Method 10 mg of the dihydroartemisinin dimer phosphatidylcholine of Embodiment 1 and 3 mg of mefloquine were dissolved in 10 ml of methanol, a solvent was removed by rotary evaporation, and then 10 ml of PBS buffer (pH 7.4) was added and shaken at 50° C. for 10 min. Finally, the mixture was filtered with a filter membrane of 0.22 micron to obtain a liposome nanoparticle solution of dihydroartemisinin dimer phosphatidylcholine loaded with mefloquine. A particle size analysis result was that an average particle size of nanoparticles was 170 nm.

Experiment Example 22

Preparation of a Liposome of Dihydroartemisinin Dithiodiglycolic Acid Dimer Phosphatidylcholine Loaded with all-Trans Retinoic Acid 10 mg of the dihydroartemisinin dithiodiglycolic acid dimer phosphatidylcholine of Embodiment 2 and 3 mg of all-trans retinoic acid were dissolved in 10 ml of methanol, a solvent was removed by rotary evaporation, and then 10 ml of PBS buffer (pH 7.4) was added and shaken at 50° C. for 10 min. Finally, the mixture was filtered with a filter membrane of 0.22 micron to obtain a liposome solution of dihydroartemisinin dithiodiglycolic acid dimer phosphatidylcholine loaded with all-trans retinoic acid. A particle size analysis result was that an average particle size of the nanoparticles was 185 nm.

Experiment Example 23

Preparation of a Liposome of Dihydroartemisinin Dithiodiglycolic Acid Dimer Phosphatidylcholine Loaded with Taxol 10 mg of the dihydroartemisinin dithiodiglycolic acid dimer phosphatidylcholine of Embodiment 2 and 2 mg of taxol were dissolved in 10 ml of methanol, a solvent was removed by rotary evaporation, and then 10 ml of PBS buffer (pH 7.4) was added and shaken at 50° C. for 10 min. Finally, the mixture was filtered with a filter membrane of 0.22 micron to obtain a liposome solution of dihydroartemisinin dithiodiglycolic acid dimer phosphatidylcholine loaded with taxol. A particle size analysis result was that an average particle size of the nanoparticles was 185 nm.

Experiment Example 24

Plasmodium Killing Test of a Liposome of Dihydroartemisinin Dimer Phosphatidylcholine Method: a plasmodium killing effect of a sample measured by a SYBR Green I fluorescence method Drug Sample:

a) The liposome of dihydroartemisinin dimer phosphatidylcholine (Embodiment 11), PBS solution, pH 7.4, and concentration: 5000 nM, 1000 nM, 200 nM, 40 nM, 8.0 nM, 1.6 nM and 0.32 nM b) Artesunate, and sodium bicarbonate solution c) The dihydroartemisinin dimer phosphatidylcholine (Embodiment 1) and PBS solution (10% DMSO)

Material: human erythrocyte infected by plasmodium strain (3D7) (0.5% parasitemia), RPMI 1640 complete medium, and carbon dioxide incubator (5% $CO_2$, 5% $O_2$, equilibrium $N_2$, and 37° C.)

100 μL of drug samples containing a medium (at an equimolar artesunate dosage) were added into a 96-well plate, and then 100 μL of erythrocytes infected by plasmodium (0.5% parasitemia) were added into each well. The medium was blank. The erythrocytes were incubated in a carbon dioxide incubator for 48 h (37° C.). Then, 50 μL of lysis buffer (containing SYBR Green I) was added into each well under a dark condition, incubation was continued for 30 min, a fluorescence intensity was measured, data were non-linearly fitted by GraphPad Prism (GraphPad Software, Inc., San Diego, Calif.), and a value of $IC_{50}$ was calculated (n=3).

Figure 17:
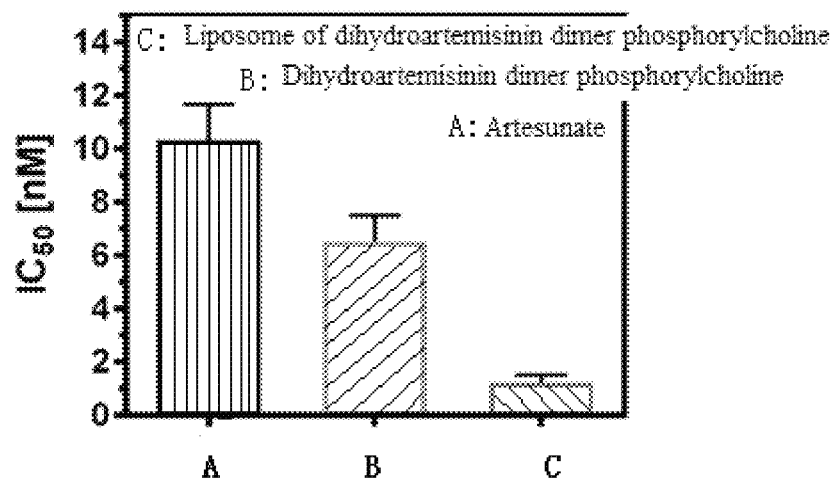
FIG. 17 illustrates values of median inhibitory concentrations IC50 of different drugs in killing plasmodium.

Result: values of median inhibitory concentrations $IC_{50}$ of different samples for killing plasmodium are shown in FIG. 17. The results show that $IC_{50}$ of the artesunate is 10.3 nM, $IC_{50}$ of the dihydroartemisinin dimer phosphatidylcholine is 6.5 nM, and $IC_{50}$ of the liposome of dihydroartemisinin dimer phosphatidylcholine is 1.2 nM. The results show that a plasmodium killing effect of the dihydroartemisinin dimer phosphatidylcholine is significantly better than that of the artesunate, and a drug efficacy of the liposome of dihydroartemisinin dimer phosphatidylcholine on killing plasmodium is about nine times that of the artesunate, showing a particularly efficient plasmodium killing effect. This is because that the liposome nanoparticles of dihydroartemisinin dimer phosphatidylcholine efficiently enter the erythrocyte using "new permeability pathways" (NPPs) on a surface of the erythrocyte infected by plasmodium, so as to kill the plasmodium.

Experiment Example 25

Plasmodium Killing Test of a Liposome of Dihydroartemisinin Dithiodiglycolic Acid Dimer Phosphatidylcholine Method: a plasmodium killing effect of a sample measured by a SYBR Green I fluorescence method Drug Sample:

a) The liposome of dihydroartemisinin dithiodiglycolic acid dimer phosphatidylcholine (Embodiment 14), PBS solution, pH 7.4, and concentration: 5000 nM, 1000 nM, 200 nM, 40 nM, 8.0 nM, 1.6 nM and 0.32 nM b) Artesunate, and sodium bicarbonate solution c) The dihydroartemisinin dithiodiglycolic acid dimer phosphatidylcholine (Embodiment 2) and PBS solution d) The dihydroartemisinin dithiodiglycolic acid dimer carboxyl betaine (Embodiment 3) and PBS solution e) PBS solution of the nanoparticles of dihydroartemisinin dithiodiglycolic acid dimer carboxyl betaine (Embodiment 15)

f) The liposome of dihydroartemisinin dimer phosphatidylcholine loaded with mefloquine (Embodiment 21)

Material: human erythrocyte infected by plasmodium strain (3D7) (0.5% parasitemia), RPMI 1640 complete medium, and carbon dioxide incubator (5% $CO_2$, 5% $O_2$, equilibrium $N_2$, and 37° C.)

100 μL of drug samples containing a medium (at an equimolar artesunate dosage) were added into a 96-well plate, and then 100 μL of erythrocytes infected by plasmodium (0.5% parasitemia) were added into each well. The medium was blank. The erythrocytes were incubated in a carbon dioxide incubator for 48 h (37° C.). Then, 50 μL of lysis buffer (containing SYBR Green I) was added into each well under a dark condition, incubation was continued for 30 min, a fluorescence intensity was measured, data were non-linearly fitted by GraphPad Prism (GraphPad Software, Inc., San Diego, Calif.), and a value of $IC_{50}$ was calculated (n=3).

Result: values of median inhibitory concentrations $IC_{50}$ of different samples for killing plasmodium are respectively that: $IC_{50}$ of the artesunate is 10.3 nM, $IC_{50}$ of the dihydroartemisinin dithiodiglycolic acid dimer phosphatidylcholine is 5.4 nM, and $IC_{50}$ of the liposome of dihydroartemisinin dithiodiglycolic acid dimer phosphatidylcholine is 0.8 nM. $IC_{50}$ of the dihydroartemisinin dithiodiglycolic acid dimer carboxyl betaine is 7.6 nM, $IC_{50}$ of the nanoparticles of dihydroartemisinin dithiodiglycolic acid dimer carboxyl betaine is 1.0 nM, and $IC_{50}$ of the liposome of dihydroartemisinin dimer phosphatidylcholine loaded with mefloquine is 0.6 nM.

The results show that a plasmodium killing effect of the dihydroartemisinin dithiodiglycolic acid dimer phosphatidylcholine is significantly better than that of the artesunate, and a drug efficacy of the liposome of dihydroartemisinin dithiodiglycolic acid dimer phosphatidylcholine on killing plasmodium is about 12 times that of the artesunate, showing a particularly efficient plasmodium killing effect. A plasmodium killing effect of the dihydroartemisinin dithiodiglycolic acid dimer carboxyl betaine is significantly better than that of the artesunate, and a drug efficacy of the nanoparticles of dihydroartemisinin dithiodiglycolic acid dimer carboxyl betaine on killing plasmodium is about 10 times that of the artesunate, showing a particularly efficient plasmodium killing effect. The liposome of dihydroartemisinin dimer phosphatidylcholine loaded with mefloquine has the lowest $IC_{50}$, which shows the optimal anti-malaria effect, and indicates that the mefloquine has a synergistic anti-malaria function.

Experiment Embodiment 26

Human Cancer Cell Killing Test by MTT Method

Drug and reagent: fetal bovine serum from the product of Nanjing SunShine Biotechnology Co., Ltd.; analytical pure of DMSO; and RPM11640 from GIBCO product.

Instrument: BIORAD 680 microplate reader.

Well-growing tumor cells were collected, a RPM11640 medium containing 10% fetal bovine serum was used to prepare 1×10-4/mL cell suspension, the tumor cells were inoculated in a 96-well culture plate, and 100 μL of the cell suspension (containing 1000 tumor cells) was added into each well, cultured in 5% $CO_2$ incubator at 37° C. for 24 h, and then added with drugs (see Table 2). Blank control and solvent control were set in the experiment, and tested samples were set with four concentrations, with three parallel wells for each concentration, and cultured in 5% $CO_2$ incubator at 37° C. for 4 days. A culture solution was discarded, and 100 μL of MTT solution (0.4 mg/mL, RPM11640 preparation) was added into each well and incubated at 37° C. for 4 h. A supernatant was discarded, 150 μL of MTT solution was added into each well to dissolve particles, and after slight shaking, an OD value was measured at a detection wavelength of 540 nm and a reference wavelength of 450 nm with a 550 microplate reader.

Result calculation: a dose-response curve can be obtained by plotting different concentrations of drugs and inhibition rates to cells, from which the median inhibitory concentration ($IC_{50}$) can be obtained, and results are shown in Table 2. From in-vitro anti-tumor activity screening, the median inhibitory concentration of the liposome of dihydroartemisinin dimer phosphatidylcholine of the present invention is higher than that of the artesunate. This is probably because that the artesunate is released slowly. The median inhibitory concentration of the liposome of dihydroartemisinin dithiodiglycolic acid dimer phosphatidylcholine is lower than that of the artesunate, which shows a strong anti-tumor effect. This is because that a disulphide bond is rapidly broken under an action of intracellular glutathione to release original drugs of the artesunate.

The liposome of dihydroartemisinin dithiodiglycolic acid dimer phosphatidylcholine and the liposome of dihydroartemisinin dimer phosphatidylcholine have a good apoptosis-inducing effect on human promyelocytic leukemia cells, and are obviously superior to the artesunate. The liposome of dihydroartemisinin dithiodiglycolic acid dimer phosphatidylcholine loaded with all-trans retinoic acid has the optimal effect on killing leukemia cells, which shows that the loaded all-trans retinoic acid has the function of synergistically killing the leukemia cells.

The liposome of dihydroartemisinin dithiodiglycolic acid dimer phosphatidylcholine loaded with taxol has the optimal effect on killing human breast cancer cells, human liver cancer cells and human lung adenocarcinoma cells, which shows that the loaded taxol has the function of synergistically killing tumor cells.

TABLE 2

Results of Killing Activity of the Compound of the Present Invention on Human Tumor Cell Strains and Leukemia Cell Strains

| Drug | $IC_{50}$ (μg/mL) | | | | |
|---|---|---|---|---|---|
| | MCF-7 | Hep G2 | A549 | HeLa | HL-60 |
| Artesunate | 150 | 100 | 110 | 130 | 130 |
| Liposome of dihydroartemisinin dimer phosphatidylcholine (Embodiment 11) | 160 | 120 | 130 | 150 | 110 |
| Liposome of dihydroartemisinin dithiodiglycolic acid dimer phosphatidylcholine (Embodiment 14) | 120 | 90 | 96 | 105 | 95 |
| Liposome of dihydroartemisinin dithiodiglycolic acid dimer phosphatidylcholine loaded with all-trans retinoic acid (Embodiment 22) | 100 | 60 | 80 | 95 | 50 |
| Liposome of dihydroartemisinin dithiodiglycolic acid dimer phosphatidylcholine loaded with taxol (Embodiment 23) | 60 | 50 | 70 | 80 | 60 |

MCF-7: human breast cancer cells;
Hep G2: human liver cancer cells;
A549: human lung adenocarcinoma cells;
HeLa: normal human vascular endothelial cells; and
HL-60: human promyelocytic leukemia cells.

Experiment Embodiment 27

In-Vivo Toxicity Test of a Mouse

Animal: ICR mouse, male, 18 g to 22 g, purchased from Vital River Laboratory Animal Technology Co., Ltd.

Oral administration: results of the in-vivo toxicity test of the compound of the present invention (Table 3) show that an oral median lethal dose is more than 2000 mg/kg, which indicates that the toxicity is far lower than that of dihydroartemisinin.

TABLE 3

Toxicity Test Results of Drugs in Mouse

| Drug | Oral median lethal dose (mg/kg weight) |
|---|---|
| Dihydroartemisinin | 810 |
| Dihydroartemisinin dimer phosphatidylcholine (Embodiment 1) | >2000 |
| Dihydroartemisinin dithiodiglycolic acid dimer phosphatidylcholine (Embodiment 2) | >2000 |

Experiment Embodiment 28

Animal Test on Treating Systemic Lupus Erythematosus with a Liposome of Dihydroartemisinin Dimer Phosphatidylcholine In preparation of a lupus model of a MRL/lpr mouse (literature: Liang Tao, etc., Chinese Journal of Immunology, 2013, 29 (3): 288-291), the MRL/lpr mouse was a gene mutation mouse with abnormal Fas expression, which leaded to excessive proliferation of lymphocytes and a systemic lupus erythematosus-like change, and was used as a model mouse of systemic lupus erythematosus (SLE).

12 female MRL/lpr mice of eight weeks old were taken as lupus model mice and randomly divided into four groups (a blank group, a dihydroartemisinin group, a group of the dihydroartemisinin dimer phosphatidylcholine of Embodiment 1, and a group of the liposome of dihydroartemisinin dimer phosphatidylcholine of Embodiment 11), with three mice in each group, one of the groups did not undergo any treatment, another two groups received intravenous injection of 2 mg (same molar weight of dihydroartemisinin) of drugs once every two days, and six female C57BL/6 mice of the same week age were additionally taken as a normal control group. The mice were put to death after eight weeks to take blood and tissues.

Blood of the mouse was taken, levels of an anti-ds-DNA antibody and an anti-nuclear antibody (ANA) in serum were measured by an ELISA kit, and specific operation steps were according to the description. Urine of the mouse was taken, a urine protein concentration of the mouse was detected by a BCA kit method, the urine protein concentration was detected with BCA, and specific operation steps were according to the description.

Pathological observation of mouse kidney: a mouse kidney tissue was fixed with 10% neutral formalin solution to make a paraffin section, hematoxylin-eosin staining (HE staining) was performed on the section, and the section was observed under microscope and photographed.

Result: after eight weeks, a spleen of the MRL/lpr mouse in the liposome group is the smallest, and a spleen of the MRL/lpr mouse in the dihydroartemisinin group is larger than that of the mouse in the normal control group, but significantly decreased compared with the untreated group. Levels of anti-ds-DNA antibody and anti-nuclear antibody (wherein the anti-ds-DNA antibody is related to an activity of lupus diseases): after eight weeks, the levels of the two autoantibodies of the MRL/lpr mouse after onset of disease are significantly higher than those of the mouse in the normal control group, the level of the anti-ds-DNA antibody of the mouse in the liposome group is significantly lower than that of the mouse in the dihydroartemisinin group and the untreated group, but the level of the anti-nuclear antibody is not changed significantly.

Nephritis change can also occur to the MRL/lpr mouse after onset of disease, and the renal pathology is manifested as: increased number of intraglomerular cells, mesangial cell proliferation, and infiltration of a large number of lymphocytes in renal interstitium. After eight weeks, the number of intraglomerular cells and the lymphocyte infiltration of the mouse in the liposome group are reduced, and are lower than those of the mouse in the dihydroartemisinin group and the dihydroartemisinin dimer phosphatidylcholine group, but the number of intraglomerular cells and the lymphocyte infiltration of the mouse in the dihydroartemisinin group are higher than those of the mouse in the dihydroartemisinin dimer phosphatidylcholine group. With occurrence of nephritis, the urine protein concentration of the MRL/lpr mouse is significantly higher than that of the mouse at the same age in the normal control group. After eight weeks, the urine protein level of the mouse in the liposome group is equivalent to that of the mouse in the normal control group; the urine protein level of the mouse in the dihydroartemisinin dimer phosphatidylcholine group is higher than that of the mouse in the normal control group, but lower than that of the mouse in the dihydroartemisinin group; and although the urine protein level of the mouse in the dihydroartemisinin group is still higher than that of the mouse in the normal control group, the urine protein level is decreased compared with the untreated group.

Conclusion: a therapeutic effect of the liposome of dihydroartemisinin dimer phosphatidylcholine on the MRL/lpr mouse is better than that of the dihydroartemisinin dimer phosphatidylcholine, and the therapeutic effect of the dihydroartemisinin dimer phosphatidylcholine is better than that of the dihydroartemisinin.

Experiment Embodiment 29

Effect of a Liposome of Dihydroartemisinin Dimer Phosphatidylcholine on an Animal with Psoriasis Preparation of animal model with psoriasis (reference): 36 mice were randomly divided into three groups, with 12 mice in each group, comprising a normal group and an imiquimod (IMQ) group. Propranolol cream was applied on a back of a mouse in a propranolol group; imiquimod cream was applied on a back of a mouse in the imiquimod group; and blank cream base was applied on a back of a mouse in the normal group, with an applying area of 1 $cm^2$ twice a day, and 3 mg of the cream each time for 8 days. Erythema, scale and thickening occurred to skin of the mouse in the imiquimod animal model group; after applying for 7 days to 8 days, the erythema changed from a pale pink spot to a dark red and brown patch gradually, and the scale changed from sporadic appearance to layered dense accumulation; and obvious infiltration occurred to the thickening of the skin.

15 imiquimod model mice prepared were randomly divided into three groups, with five mice in each group: a group of the liposome of dihydroartemisinin dimer phosphatidylcholine of Embodiment 11, a dihydroartemisinin group (PBS solution, dosage 3 mg/20 g weight, and same molar weight of dihydroartemisinin), a model control group and a negative control group. Normal saline was applied on a back of a mouse in the negative control group; a back of a mouse in the model control group did not undergo any treatment; the liposome of dihydroartemisinin dimer phosphatidylcholine and the dihydroartemisinin were respectively applied to the mouse in the administration group twice a day for 8 consecutive days to observe a skin change.

Result: compared with the model group and the negative control group, a skin lesion symptom of the mouse in the group of the liposome of dihydroartemisinin dimer phosphatidylcholine is obviously relieved, and back skin of the mouse becomes smooth and delicate, on which the scales are obviously reduced, a color of the erythema becomes pale, and a thickening degree of skin is reduced. A skin lesion symptom of the mouse in the dihydroartemisinin group is also improved, but is not as obvious as that of the mouse in the liposome group. Results show that the liposome of dihydroartemisinin dimer phosphatidylcholine has the best effect on repairing skin injury.

Experiment Embodiment 30

Effect of a Liposome of Dihydroartemisinin Dimer Phosphatidylcholine on an Animal Model with Rheumatoid Arthritis Animal model: a rat of 2 months to 3 months old with a weight of 160 g to 180 g was provided by the Experimental Animal Center of Nanjing Medical University, II-type collagen of the rat was dissolved in 0.1 mol/L acetic acid solution, stirred at 4° C. to be fully dissolved with a concentration of 2 g/L, and placed in a refrigerator at 4° C. overnight, and then an inactivated *Bacillus* Calmette-Guerin vaccine (BCG) was placed in liquid paraffin to be prepared into 2 g/L complete Freund's adjuvant, and the mixture and the Freund's adjuvant were mixed in equal volume and emulsified to be prepared into a CII emulsion. The emulsion was intradermally injected into a tail root of a mouse to induce inflammation, and 0.1 ml of the emulsion was intraperitoneally injected for 21 days as excitation injection. The mouse developed joint swelling 24 days after the inflammation and reached a peak 36 days after the inflammation, a change of foot claws was measured by a foot claw meter, and if the foot claws were significantly larger than those of the mouse in the normal control group ($P<0.01$) 28 days after the inflammation, the modeling was successful.

16 rats were randomly divided into a normal group, a model group, a group of the liposome of dihydroartemisinin dimer phosphatidylcholine of Embodiment 11 and a dihydroartemisinin group (PBS solution, dosage 3 mg/20 g weight, and same molar weight of dihydroartemisinin), with four rats in each group. Normal saline was given to a negative control group; the model control group did not undergo any treatment; and an administration group received intravenous injection of a liposome of dihydroartemisinin dimer phosphatidylcholine and a dihydroartemisinin PBS solution once every two days for 20 consecutive days. According to the reference method (Journal of Beijing University of Traditional Chinese Medicine, 2014, 37(3), 190), a swelling degree of a foot sole of the rat, contents of interleukin-1 and interleukin-2 (IL-1 and IL-2) of serum, and protein expressions of an apoptosis inhibitor gene (Bcl-2) of a synovial tissue of a joint and a cysteine protease (Caspase-3) were observed.

Result: acute inflammatory redness and swelling occurs the foot sole and ankle of the model rat, a foot sole circumference is significantly thicker than that of the rat in the normal group, the content of IL-1 in serum is increased, a level of IL-2 is decreased, and the protein expressions of Bcl-2 and Caspase-3 are both increased ($P<0.05$). After administration, a foot sole circumference of the rat in the group of the liposome of dihydroartemisinin dimer phosphatidylcholine is decreased, the content of IL-1 in serum is decreased, the level of IL-2 is increased, the protein expression of Bcl-2 is decreased significantly ($P<0.05$), and the protein expression of Caspase-3 is increased ($P<0.05$). An effect of the dihydroartemisinin group is slightly worse, but the indexes are better than those of the positive control group without administration. Therefore, the liposome of dihydroartemisinin dimer phosphatidylcholine has a better therapeutic effect on rheumatoid arthritis.

Embodiment 31

Preparation of Nanoparticles of a Dihydroartemisinin Dimer Derivative by a Thin Film Method 10 mg of the dihydroartemisinin dimer serinol hydrochloride of Embodiment 4, 10 mg of the dihydroartemisinin dithiodiglycolic acid dimer hydroxysulfobetaine of Embodiment 5, 10 mg of the dihydroartemisinin diglycolic acid dimer phosphatidylcholine of Embodiment 6, 10 mg of the dihydroartemisinin dithiodiglycolic acid dimer sulfobetaine of Embodiment 7, 10 mg of the dihydroartemisinin diethyldithiocarbamate acid ester dimer phosphatidylcholine of Embodiment 8, 10 mg of the dihydroartemisinin dithiodiglycolic acid dimer—N,N-dimethylamino hydrochloride of Embodiment 9, and 10 mg of the dihydroartemisinin dithiodiglycol carbonic ester dimer serinol hydrochloride of Embodiment 10 were respectively dissolved in 10 ml of chloroform, a solvent was removed by rotary evaporation, and then 10 ml of PBS buffer (pH 7.4) was added and shaken at 50° C. for 10 min. The mixture was filtered with a filter membrane of 0.22 micron to obtain nanoparticle solutions of dihydroartemisinin dimer serinol hydrochloride, dihydroartemisinin dithiodiglycolic acid dimer hydroxysulfobetaine, dihydroartemisinin diglycolic acid dimer phosphatidylcholine, dihydroartemisinin dithiodiglycolic acid dimer sulfobetaine, dihydroartemisinin diethyldithiocarbamate acid ester dimer phosphatidylcholine, dihydroartemisinin dithiodiglycolic acid dimer—N,N-dimethylamino hydrochloride and dihydroartemisinin dithiodiglycol carbonic ester dimer serinol hydrochloride. A particle size was analyzed by a dynamic light scattering instrument, and was between 150 nm and 300 nm. The morphology of the nanoparticles was measured by transmission electron microscope, and was spherical.

The embodiments above are only the preferred embodiments of the present invention, and it should be noted that those of ordinary skills in the art can made several improvements and equivalent substitutions without departing from the principle of the present invention, and these technical solutions after the improvements and equivalent substitutions made to the claims of the present invention are all included within the protection scope of the present invention.

What is claimed is:

1. A method for treating parasitosis, autoimmune disease, tumor, leukemia, toxoplasmosis or skin disease comprising a step of administrating a dihydroartemisinin dimer derivative to a subject in need of treatment;

wherein the dihydroartemisinin dimer derivative has a general formula (1) or a pharmaceutically acceptable salt thereof:

formula (I)

$$\text{artemisinin structure}-O-\overset{O}{\underset{\|}{C}}-X-\overset{O}{\underset{\|}{C}}-O-\overset{}{\underset{Y}{CH}}-$$

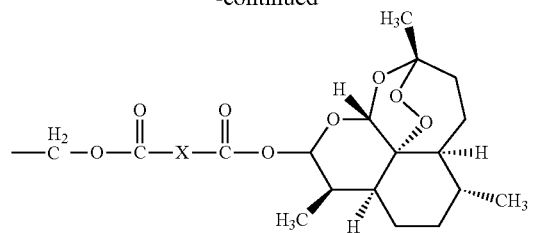

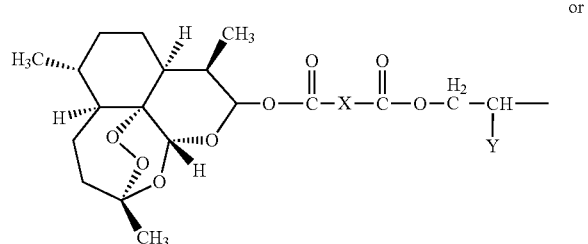

or

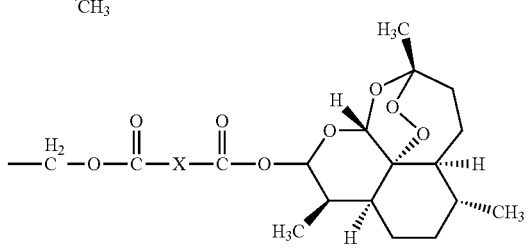

wherein X is selected from a group consisting of CH$_2$, CH$_2$—CH$_2$, CH$_2$—CH$_2$—CH$_2$, CH$_2$—CH$_2$—CH$_2$—CH$_2$, CH$_2$—S—S—CH$_2$, CH$_2$—CH$_2$—S—S—CH$_2$—CH$_2$, CH$_2$—O—CH$_2$, O—CH$_2$—CH$_2$—O, O—CH$_2$—CH$_2$—CH$_2$—O, O—CH$_2$—CH$_2$—CH$_2$—CH$_2$—O, O—CH$_2$—CH$_2$—O—CH$_2$—CH$_2$—O, O—CH$_2$—CH$_2$—O—CH$_2$—CH$_2$—O—CH$_2$—CH$_2$—O, O—CH$_2$—CH$_2$—SS—CH$_2$—CH$_2$—O—CO—CH$_2$—CH$_2$, O—CH$_2$—CH$_2$—CH$_2$—CH$_2$—O—CO—CH$_2$—CH$_2$, O—CH$_2$—CH$_2$—CH$_2$—CH$_2$—CH$_2$—CH$_2$—O—CO—CH$_2$—CH$_2$, O—CH$_2$—CH$_2$—CH$_2$—O—CO—CH$_2$—CH$_2$, NH—CH$_2$—CH$_2$—NH, NH—CH$_2$—CH$_2$—CH$_2$—NH, NH—CH$_2$—CH$_2$—CH$_2$—CH$_2$—NH, NH—CH$_2$—CH$_2$—CH$_2$—CH$_2$—CH$_2$—NH, NH—CH$_2$—CH$_2$—CH$_2$—CH$_2$—CH$_2$—CH$_2$—NH, O—CH$_2$—CH$_2$—S—S—CH$_2$—CH$_2$—O and NH—CH$_2$—CH$_2$—S—S—CH$_2$—CH$_2$—NH;

and Y is selected from a group consisting of

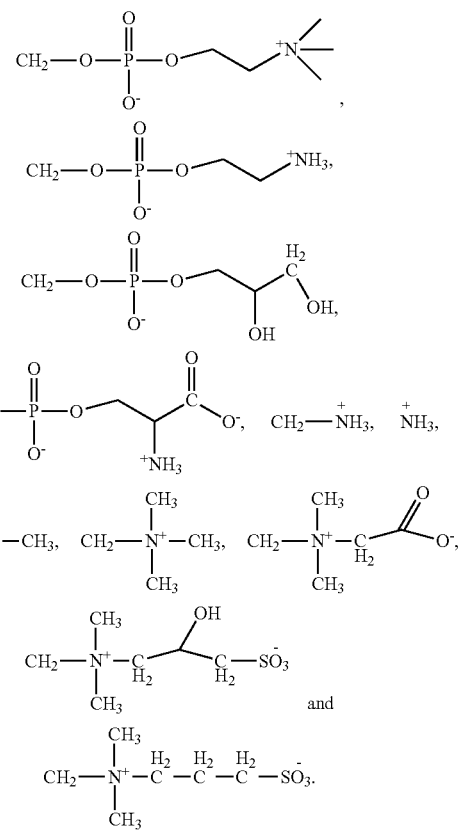

2. The method according to claim 1, wherein the parasitosis is selected from a group consisting of malaria, schistosomiasis, toxoplasmosis, leishmaniasis, filariasis and ancylostomiasis.

3. The method according to claim 1, wherein the autoimmune disease is selected from a group consisting of systemic lupus erythematosus, rheumatoid arthritis, systemic vasculitis, pemphigus, mixed connective tissue disease, autoimmune hemolytic anemia, thyroid autoimmune disease and ulcerative colitis.

\* \* \* \* \*